United States Patent [19]

Bercaw et al.

[11] Patent Number: 5,708,101
[45] Date of Patent: Jan. 13, 1998

[54] STEREOSPECIFIC OLEFIN POLYMERIZATION CATALYSTS

[75] Inventors: John E. Bercaw; Timothy A. Herzog, both of Pasadena, Calif.

[73] Assignee: California Institute of Technology, Pasadena, Calif.

[21] Appl. No.: 696,004

[22] Filed: Aug. 12, 1996

Related U.S. Application Data

[60] Provisional application No. 60/002,419, Aug. 17, 1995.
[51] Int. Cl.$^6$ .................................................... C08F 4/642
[52] U.S. Cl. ..................... 526/127; 526/160; 526/170; 526/943; 526/351; 502/102; 502/103; 502/117; 502/152; 556/11; 556/43; 556/53; 556/87; 534/15
[58] Field of Search .............................. 526/127, 160, 526/170, 943; 502/102, 103, 117, 152; 556/11, 43, 53, 87; 534/15

[56] References Cited

U.S. PATENT DOCUMENTS 5,459,117  10/1995  Ewen ..................................... 502/117
5,496,902  3/1996  Evertz et al. ......................... 526/127

OTHER PUBLICATIONS

Ewen, John A., et al., Syndiospecific Propylene Polymerizations with Group 4 Metallocenes, *J. Am. Chem. Society*, 110, 6255–6256 (1988).
Mengele, Winfried, et al., ansa–Metallocene Derivatives.27 Chiral Zirconocene Copleses with Two Dimethylsilylene Bridges, *Organometallics*, 12, 1931–1935 (1993).
Brintzinger, Hans H., et al., Stereospecific Olefin Polymerization with Chiral metallocene Catalysts, *Angew. Chem. Int. Ed. Engl.*, 34, 1143, 1152, 1153, 1156 (1995).
Cano, A., et al. Double–Dimethylsilyl–Bridged Dicyclopentadienyl Group 4 Metal Complexes. *Organometallics*, 13, 1688–1694 (1994).
Lang, H., Untersuchungen von Polymerisations—und Metathesereaktionen, XXII. *Journal of Organometallic Chemistry*, 490, C32–C36 (1995).
Bulls, Al Ray—Thesis: "Carbon–Hydrogen Bond Activation by Peralkylhafnocene and Peralkylscandocene Derivatives", Chapter 3, 64–79 (1988).
Cano, Ana, et al.—Dicyclopentadienyl Titanium and Zirconium Complexes, With the Double Bridged bis(dimethylsilanodiyl) Dicyclopentadienyl, etc.; *J. Org. Chem.*, 526, 227–235 (1996).
Cavallo, Luigi, et al. —Doubly Bridged ansa–Zirconocenes Based on the Norbornadiene Skeleton: A Quantum Mechanical and Molecular Mechanics Study; *Organometallics*, 15, 2254–2263 (1996).
Dorer, Birgit, et al.—Syntheses and Structures of Titanocene, Zirconocene, and Vanadocene Dichloride Complexes with Two Ethanediyl Bridges; *Organometallics*, 13, 3868–3872 (1994).
Fernández, Francisco J., et al., β–Hydrogen–Containing Zirconium Alkyls, with the Doubly–Bridged Bis(dimethylsilanediyl)dicyclopentadienyl Ligand; *Organometallics*, 16, 1553–1561 (1997).
Grossman, Robert B., et al., Synthesis and Structure of a $C_2$–Symmetric, Doubly Bridged ansa–Titanocene Complex; *Organometallics*, 13, 3892–3896 (1994).
Hafner, Klaus, et al., Synthesis and Structure of the First [$2_2$]Metallocenophanes; *Angew. chem. Int. Ed. Engl.*, 33 No. 14, 1479–1480 (1994).
Hiermeier, Johann, et al., Limiting the Relative Orientation of Bridged Cyclopentadienyl Anions; *Organometallics*, 10, 1787–1793 (1991).
Huhmann, Jean L., et al., Synthesis of New Silyl–Bridged Bis(cyclopentadienyl) Ligands and Complexes; *Organometallics*, 15, 4063–4074 (1996).
Hüttenhofer, Mario, et al., Substituted Silastannatetrahydro–s–indacenes as Cyclopentadienyl, Transfer Agents in the Synthesis of Silanediyl–Bridged zirconocene Complexes; *Organometallics*, 15, 4816–4822 (1996).

(List continued on next page.)

*Primary Examiner*—Mark Nagumo
*Attorney, Agent, or Firm*—Limbach & Limbach L.L.P.

[57] ABSTRACT

A metallocene catalyst system for the polymerization of α-olefins to yield stereospecific polymers including syndiotactic, and isotactic polymers. The catalyst system includes a metal and a ligand of the formula

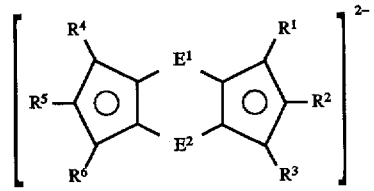

wherein: $R^1$, $R^2$, and $R^3$ are independently selected from the group consisting of hydrogen, $C_1$ to $C_{10}$ alkyl, 5 to 7 membered cycloalkyl, which in turn may have from 1 to 3 $C_1$ to $C_{10}$ alkyls as a substituent, $C_6$ to $C_{15}$ aryl or arylalkyl in which two adjacent radicals may together stand for cyclic groups having 4 to 15 carbon atoms which in turn may be substituted, or $Si(R^8)_3$ where $R^8$ is selected from the group consisting of $C_1$ to $C_{10}$ alkyl, $C_6$ to $C_{15}$ aryl or $C_3$ to $C_{10}$ cycloalkyl; $R^4$ and $R^6$ are substituents both having van der Waals radii larger than the van der Waals radii of groups $R^1$ and $R^3$; $R^5$ is a substituent having a van der Waals radius less than about the van der Waals radius of a methyl group; $E^1$, $E^2$ are independently selected from the group consisting of $Si(R^9)_2$, $Si(R^9)_2—Si(R^9)_2$, $Ge(R^9)_2$, $Sn(R^9)_2$, $C(R^9)_2$, $C(R^9)_2—C(R^9)_2$, where $R^9$ is $C_1$ to $C_{10}$ alkyl, $C_6$ to $C_{15}$ aryl or $C_3$ to $C_{10}$ cycloalkyl; and the ligand may have $C_S$ or $C_1$-symmetry. Preferred metals are selected from the group consisting of group III, group IV, group V or lanthanide group elements. The catalysts are used to prepare stereoregular polymers including polypropylene from α-olefin monomers.

35 Claims, No Drawings

OTHER PUBLICATIONS

Jones, Paul Ronald, et al., Silenes and Silenoids; *Organometallics*, 4, 1321–1324 (1985).

Lang, H., et al., Synthesis and Reaction Behavior of the Novel Mono(σ–alkynyl)titanocene Chloride, etc.; *Organometallics*, 14, 1850–1854 (1995).

Mansel, Stefan, et al., ansa–Metallocene Derivatives XXXII; *J. Org. Chem.*, 512, 225–236 (1996).

Nakadaira, Yasuhiro, et al., 6,6–Dimethyl–6–Silafulvene. Generation and Trapping Reactions; *Chemistry Letters*, pp. 1071–1074 (1980).

Siemelling, Ulrich, et al., Binuclear Metal Complexes of a Doubly Bridged Cyclopentadienyl Ligand; *Organometallics*, 11, 1328–1333 (1992).

Weiss, Karin, et al., Untersuchungen von Polymerisations–und Metathesereaktionen, XXIII; *J. Org. Chem.*, 520, 171–179 (1996).

STEREOSPECIFIC OLEFIN POLYMERIZATION CATALYSTS

This application claims the benefit of U.S. Provisional Application No. 60/002,419, filed Aug. 17, 1995.

The U.S. Government has certain rights in this invention pursuant to Grant No. DE-FG03-85ER13431 awarded by the Department of Energy.

BACKGROUND

The present invention relates generally to olefin polymerization catalysts, and more specifically to catalysts for polymerizing α-olefins to produce stereospecific polymers.

The polymerization of olefins using homogeneous Ziegler-Natta catalysts has created tremendous interest in the past 15 years. Industrially, this interest has arisen from the very high activity and productivity of these systems as well as the favorable economics of transforming inexpensive olefins, such as ethylene and propylene, into useful polymers.

Historically, the best Ziegler-Natta catalysts were multicomponent heterogeneous mixtures of transition metal halides, alkyl aluminums and Lewis bases. However the catalytic center in these systems is ill defined and this has hampered the systematic development of new heterogeneous catalysts. The discovery of homogeneous catalysts based on metallocenes has allowed for a much better understanding of the mechanism of these important reactions and for a more rational development of new catalysts.

One class of compounds that have proved useful as olefin polymerization catalysts are metallocenes based on group III, IV, and V metals. The group IV catalysts are typically cationic while the Group III metallocene catalysts are typically neutral. The Group IV cations require a noncoordinating anion such as that derived from methylaluminoxane (MAO) or fluorophenylborates, to be active polymerization catalysts. Catalysts with Group IV metals are often extremely active and are therefore very important industrially.

There is a clear relationship between the structure and function of Ziegler-Natta metallocene catalysts for olefin polymerization. For example, most achiral catalysts, such as zirconocene dichloride, in the presence of an activating species, such as MAO, react with propylene to form atactic polypropylene, an amorphous solid with few uses.

Most $C_2$-symmetric metallocenes react with propylene to form isotactic polypropylene which is a hard translucent material with numerous applications. See for example Brinzinger et al, Angew. Chem. Intl. Ed. Engl. 34 1143 (1995).

A number of $C_1$-symmetric metallocenes have been prepared, which react with propylene to form isotactic polypropylene. See for example Rieger et al, Organometallics 13 647–653 (1994).

$C_S$-symmetric catalysts typically yield atactic polypropylene. However, a few $C_S$-symmetric catalysts based on a fluorenyl moiety yield syndiotactic polypropylene, for example the catalyst based on the isopropylidene linked fluorenyl cyclopentadienyl ligand ($^i$PrFlCp) developed by Ewen and Razavi (J. Am. Chem. Soc. 110 6255-6256, 1988). Syndiotactic polypropylene has recently been produced on a large scale and has been used as a blend with isotactic polypropylene.

It is an object of the present invention to provide a new class of metallocene based olefin polymerization catalysts that produce highly stereospecific polymers. It is a further object of the invention to provide a catalyst system that can easily be fine tuned to produce polymers with a variety of specific microstructures.

SUMMARY

The present invention provides a new catalyst system for polymerizing olefins to produce polyolefins. The catalyst includes a metal and a ligand of the formula

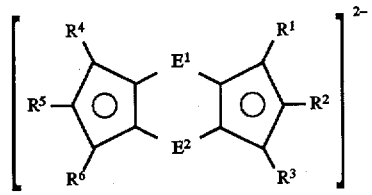

where $R^1$–$R_6$ have the following meaning.

$R^1$, $R^2$, and $R^3$ are independently selected from the group consisting of hydrogen, $C_1$ to $C_{10}$ alkyl, 5 to 7 membered cycloalkyl, which in turn may have from 1 to 3 $C_1$ to $C_{10}$ alkyls as a substituent, $C_6$ to $C_{15}$ aryl or arylalkyl in which two adjacent radicals may together stand for cyclic groups having 4 to 15 carbon atoms which in turn may be substituted, and $Si(R^8)_3$ where $R^8$ is selected from the group consisting of $C_1$ to $C_{10}$ alkyl, $C_6$ to $C_{15}$ aryl or $C_3$ to $C_{10}$ cycloalkyl.

$R^4$ and $R^6$ are substituents both having van der Waals radii larger than the van der Waals radii of groups $R^1$ and $R^3$.

$R^5$ is a substituent having a van der Waals radius that is less than the van der Waals radius of a methyl group.

$E^1$ and $E^2$ are independently selected from the group consisting of $Si(R^9)_2$, $Si(R^9)_2$—$Si(R^9)_2$, $Ge(R^9)_2$, $Sn(R^9)_2$, $C(R^9)_2$, and $C(R^9)_2$—$C(R^9)_2$, where $R^9$ is selected from the group consisting of $C_1$ to $C_{10}$ alkyl, $C_6$ to $C_{15}$ aryl, and $C_3$ to $C_{10}$ cycloalkyl.

The metal is preferably selected from the group consisting of group III, group IV, group V and lanthanide group elements, and most preferably selected from the group consisting of titanium, zirconium, hafnium, scandium, yttrium, and the lanthanides.

The preferred $R^4$ and $R^6$ groups are independently selected from the group consisting of $C_1$ to $C_{10}$ alkyl, 5 to 7 membered cycloalkyl which in turn may have a $C_1$ to $C_{10}$ alkyl as a substituent, $C_6$ to $C_{15}$ aryl or alkylaryl, and $Si(R^8)_3$.

The preferred $R^5$ group is hydrogen.

The preferred $R^2$ group is selected from the group consisting of hydrogen, methyl, ethyl, isopropyl, tert-butyl, phenyl, and trimethylsilyl.

The preferred $E^1$ and $E^2$ groups are both $Si(Me)_2$.

In one preferred embodiment of the catalyst, $R^1$ and $R^3$ are the same and are hydrogen or methyl; $R^2$ is selected from the group consisting of hydrogen, methyl, ethyl, isopropyl, tert-butyl, trimethylsilyl, and phenyl; $R^4$ and $R^6$ are the same and are selected from the group consisting of methyl, ethyl, isopropyl, tert-butyl, phenyl, —CH(Me)(Et), —CH(Me)($^t$Bu), and trimethylsilyl. In a more preferred embodiment of this class of catalyst, $R^4$ and $R_6$ are isopropyl; $E^1$ and $E^2$ are $Si(Me)_2$; $R^1$ and $R^3$ are hydrogen; and $R^2$ is selected from the group consisting of isopropyl and trimethylsilyl.

In another preferred embodiment of the catalyst, $R^1$ and $R^3$ are hydrogen, and $R^2$ is chiral.

In another preferred embodiment, $R^1$ and $R^2$ are the same and are selected from the group consisting of $C_1$ to $C_{10}$ alkyl, 5 to 7 membered cycloalkyl, which in turn may have from 1 to 3 $C_1$ to $C_{10}$ alkyls as a substituent, $C_6$ to $C_{15}$ aryl or arylalkyl in which two adjacent radicals may together stand for cyclic groups having 4 to 15 carbon atoms which in turn may be substituted, and $Si(R^8)_3$ where $R_8$ is selected from the group consisting of $C_1$ to $C_{10}$ alkyl, $C_6$ to $C_{15}$ aryl or $C_3$ to $C_{10}$ cycloalkyl; and $R^3$ is hydrogen. In a more preferred embodiment of this class of catalysts, $R^1$ and $R^2$ may be the same and are selected from the group consisting of methyl, trimethylsilyl, tert-butyl, or together form the 6 membered ring of an indenyl, or tetrahydroindenyl. In the most preferred embodiment of this class of catalysts, $R^1$ and $R^2$ together form the 6 membered ring of a tetrahydroindenyl, and $R^4$ and $R^6$ are both isopropyl.

In another preferred embodiment of the catalyst, $R^1$ and $R^3$ are hydrogen, and $R^4$ and $R^6$ are different. In a more preferred embodiment of this class of catalysts, $R^4$ is isopropyl or tert-butyl; $R^6$ is methyl; and $R^2$ is selected from the group consisting of $C_1$ to $C_{10}$ alkyl, and 5 to 7 membered cycloalkyl, which in turn may have from 1 to 3 $C_1$ to $C_{10}$ alkyls as a substituent.

The catalyst system may further include an activator. In a preferred embodiment the activator is methylaluminoxane.

The catalyst may further include n ligands independently selected from the group consisting of fluorine, chlorine, bromine, iodine, hydrogen, $C_1$ to $C_{10}$ alkyl, $C_6$ to $C_{15}$ aryl, and $—OR^7$ where $R^7$ selected from the group consisting of $C_1$ to $C_{10}$ alkyl, $C_6$ to $C_{15}$ aryl, alkylaryl, arylalkyl, fluoroalkyl, and fluoroaryl with 1 to 10 carbon atoms in the alkyl radical and 6 to 20 carbon atoms in the aryl radical. In this embodiment, n is the valence of the metal minus 2 and the catalyst may have the following structure

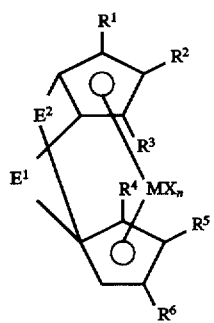

I

The invention further includes a method for polymerizing olefins comprising the step of contacting an olefin with a catalyst of the type described above. The olefin may be a $C_3$–$C_{10}$ α-olefin, and the olefin may be contacted with the catalyst in the presence of a solvent.

DETAILED DESCRIPTION

Introduction

The present invention relates to a new stereospecific olefin polymerization catalyst the general formula of which is

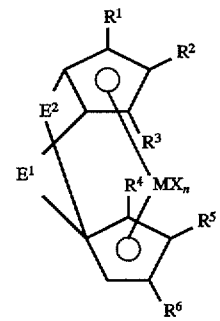

I

The inventors have discovered that by choosing a particular combination of the substituents $R^1$–$R^6$ it is possible to produce a catalyst that polymerizes olefins to yield highly stereoregular polymers. Furthermore, the inventors have discovered that by changing the $R^1$–$R^6$ groups in a well defined manner it is possible to produces polymers having very different microstructures including syndiotactic, and isotactic.

The catalysts of the present invention include the following structural characteristics:

(i) The catalysts contain an open region at the $R^5$ position. It is thought that this feature allows the polymerizing monomer to approach the catalytic center with the correct orientation to produce a polymer with the desired microstructure. The open region may be achieved by having a $R^5$ substituent that does not sterically hinder the incoming monomers. Suitable $R^5$ substituents are groups with a van der Waals radius that is less than about the van der Waals radius of a methyl group. Suitable examples are hydrogen and fluorine. A preferred example is hydrogen. The van der Waals radius of an atom or group is the effective size of the atom or group. When two atoms or groups which are not bonded together come within their van der Waals radii, strong repulsion occurs. See for example Organic Chemistry, Fourth Edition, by Stanley H. Pine et al, McGraw Hill, 1981, which is incorporated herein by reference.

(ii) The cyclopentadienyl ring bearing the open region also bears substituents $R^4$ and $R^6$ that are larger (i.e. have a larger van der Waals radius) than the $R^1$ and $R^3$ substituents on the other cyclopentadienyl ring.

(iii) The symmetry of the molecule is important in determining the microstructure of the polymer produced. Since the monomers to be polymerized are thought to approach the metal center from the open side of the metallocene wedge, the $R^1$–$R^6$ groups are expected to control the stereochemistry of the reaction. For this reason, the $E^1$ and $E^2$ groups are expected to be less important in controlling the polymerization reaction. The inventors have found that when the catalyst has $C_S$-symmetry the resulting polymer is highly syndiotactic. In contrast, when the molecule has $C_1$-symmetry, the resulting polymer may be syndiotactic, or isotactic depending on the reaction conditions and the specific substituent groups.

iv) To maintain the desired symmetry of the catalyst the cyclopentadienyl rings are doubly bridged.

One embodiment of the bis-cyclopentadienyl ligand and catalyst that includes the "open region" of the present invention is shown below

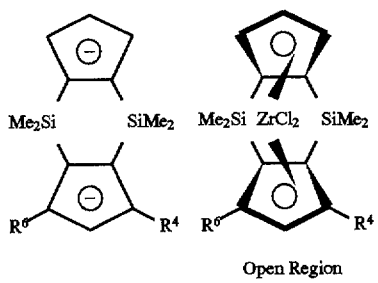

Open Region

As is shown in the examples below, the unique configuration of the substituent groups discovered by the inventors leads to a catalyst system that is highly stereospecific. Furthermore, by varying the substituent groups and the reaction conditions the catalyst system may be tuned to give polymers of different microstructure.

$C_S$-Symmetric Catalysts

The $C_S$-symmetric catalysts of the present invention have $R^1=R^3$, $R^4=R^6$, and $R^2$ achiral. As discussed above, the $E^1$ and $E^2$ groups are expected to be relatively unimportant in the activity of the catalyst and these groups are therefore not restricted to conform with the $C_S$-symmetry of the molecule.

In a preferred embodiment of the $C_S$-symmetry catalyst the $R^1$ and $R^3$ groups are hydrogen, the $R^4$ and $R^6$ groups are isopropyl, and the $R^2$ group may be varied. The activity and stereoselectivity of the catalysts depend on the form of the $R^2$ group as is shown below.

$C_1$-Symmetric Catalysts

The $C_1$-symmetric catalysts of the present invention may be of the following four types:

(i) $R^1=R^3$ and $R^2$ is chiral. In a preferred embodiment of this type of catalyst, $R^1=R^3$=hydrogen, $R^4=R_6=$ isopropyl, and $R^2$ is —CH(Me)(Et) or —CH(Me)($^t$Bu).

(ii) $R^2=R^3\neq$hydrogen and $R^1$ is hydrogen. $R^2$ and $R^3$ may be any suitable alkyl or silyl group or may together form a cyclic group such as indenyl or tetrahydroindenyl. These catalysts are expected to make isotactic polymers under most conditions. In a preferred embodiment of this class of catalysts, $R^2$ and $R^3$ together form a tetrahydroindenyl ring and $R^4=R^6=$ isopropyl.

(iii) $R^2\neq R^3$ and $R^1\neq R^3$ and $R^1$=hydrogen.

(iv) $R^4\neq R^6$. In a preferred embodiment of this type of catalyst, $R^1=R^3$=hydrogen, $R^2$ is any suitable alkyl, $R^4$ is isopropyl or tert-butyl, and $R_6$ is methyl.

Synthesis of Catalysts

The catalysts of the present invention may be prepared by a variety of methods including those shown below. Detailed descriptions of the synthetic steps and reaction conditions are given in the "Experimental Procedures" Section and in Timothy Herzog's Ph.D. thesis which is incorporated herein by reference (California Institute of Technology, Pasadena, Calif., 1996).

Synthesis of Generic Double Bridged Bis-Cyclopentadiene Ligand

The substituted cyclopentadienes can be made by known methods. The anions of the substituted cyclopentadienes are prepared by treating the substituted cyclopentadienes with alkali metal-alkyls or Grignard reagents in a solvent to give the substituted cyclopentadienide anions:

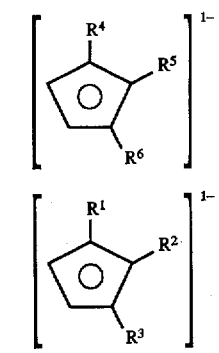

In a solvent [Cp$^1$] is treated first with $E^1X'_2$ where X' may be chlorine, bromine, iodine, or triflate to form Cp$^1$E$^1$X', which is subsequently treated with the anion of the second cyclopentadiene. [Cp$^2$]- to form Cp$^1$E$^1$Cp$^2$. Cp$^1$E$^1$Cp$^2$ is then treated with two equivalents of alkali metal-alkyl or Grignard reagent in a solvent to produce the dianion [Cp$^1$E$^1$Cp$^2$]$^{2-}$;

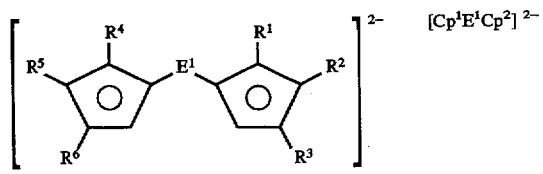

Subsequent reaction with $E^2X'_2$ in a solvent produces the doubly-bridged compound $(Cp^1)E^1/E^2(Cp^2)$ which when reacted with two equivalents of an alkali metal alkyl or Grignard reagents produces the dianion.

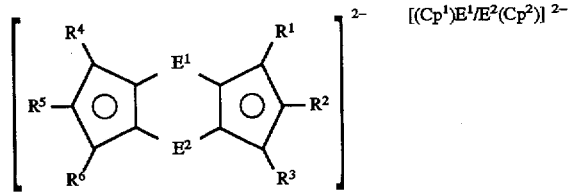

$[(Cp^1)E^1/E^2(Cp^2)]^{2-}$ reacts in a solvent with $MX_{n+2}$ or etherates of $MX_{n+2}$ to produce compound I, Synthesis of Specific Double Bridged Bis-Cyclopentadiene Ligands and Metallocene Catalysts The synthetic approach used to prepare these complexes is similar to that developed by Bulls (Ph.D. thesis, CalTech, Pasadena, Calif., 1988) and Brintzinger (Organometallics, 12 1931–1935, 1993) both of which are incorporated herein by reference. In these synthetic approaches, a singly bridged dianionic ligand is treated with dimethylsilyldichloride to form the doubly bridged protonated ligand. A difference between these synthetic approaches and that of the present invention is in the synthesis of the asymmetric singly linked ligand. The basic approach of the present invention is shown below.

Synthetic scheme for doubly bridged ligands.

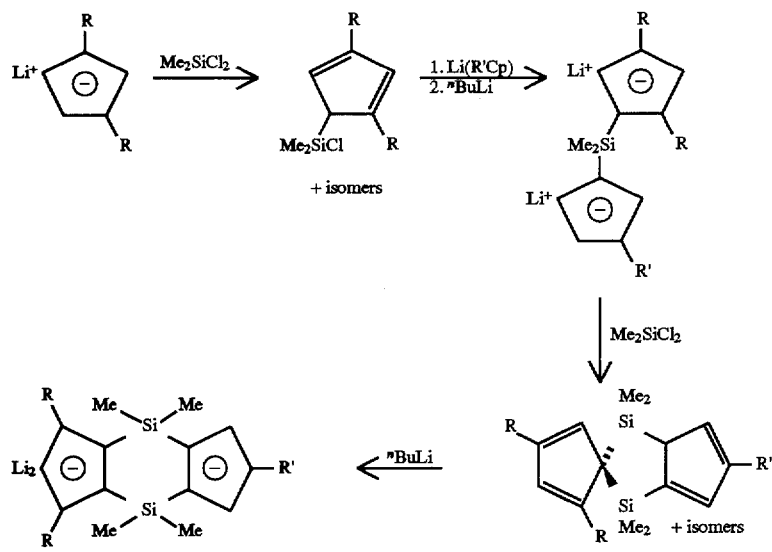

The first step in the synthesis of these types of catalysts is the synthesis of 1,3-dialkylcyclopentadienes. 1,3-di(tert-butyl) cyclopentadiene has been prepared by Casserly (J. Am. Chem. Soc. 112 2808–2809, 1990) so it was a straightforward starting point. Using this synthetic scheme, singly bridged dianionic ligands were prepared, but the second linking reaction was never successful despite considerable effort. After a molecular modeling analysis of the expected structure, it was determined that the tert-butyl groups were too bulky to allow for the linking group. For comparison, it is exceedingly difficult to prepare bulky tetrasubstituted cyclopentadienyls.

Therefore, 1,3-diisopropylcyclopentadiene was selected as the starting point for the synthesis. Unfortunately, the reported syntheses of 1,3-diisopropylcyclopentadiene gave low yields since the final step was always separation of the 1,3 product from the 1,2 product. A more selective method was found by extension of work by Nile in which he prepared a number of 1,3 disubstituted cyclopentadienes using a fulvene route. Using this method, reaction of isopropylcyclopentadiene with acetone catalyzed by pyrrolidine gave the 3-isopropyl-6,6-dimethylfulvene. Subsequent reduction of the fulvene with LAH and hydrolysis provided 1,3-diisopropylcyclopentadiene, "$^iPr_2Cp$."

Preparation of 1,3-diisopropylcyclopentadiene.

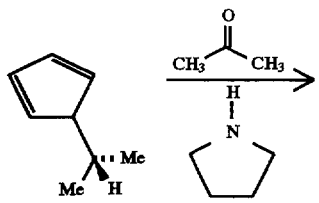

-continued
Preparation of 1,3-diisopropylcyclopentadiene.

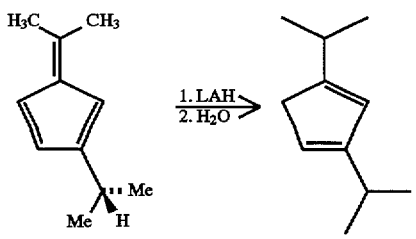

This synthesis is amenable to large scales and has been used to prepare over 400 g of 1,3-diisopropylcyclopentadiene in a single prep in 74% yield from isopropylcyclopentadiene.

1,3-diisopropylcyclopentadiene is easily deprotonated with $^n$BuLi in pentane to yield lithium(1,3-diisopropylcyclopentadienylide) "Li($^iPr_2Cp$)" in high yield. The reaction of Li($^iPr_2Cp$) with excess dichlorodimethylsilane in tetrahydrofuran at −78° C. yields ($^iPr_2Cp$)Me$_2$SiCl in over 90% yield as a yellow oil. Reaction of ($^iPr_2Cp$)Me$_2$SiCl with the lithium salt of R'Cp {R'=H, $^i$Pr, TMS, $^{sec}$Bu, or CH(Me)($^t$Bu)} yields the singly bridged ligand, "($^iPr_2Cp$)Me2Si(R'Cp)," as yellow oils which can be kugel-röhr distilled at high vacuum at 90–120° C.

Synthesis of singly bridged ligands.

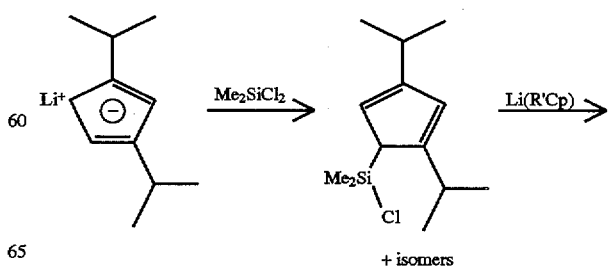

-continued
Synthesis of singly bridged ligands.

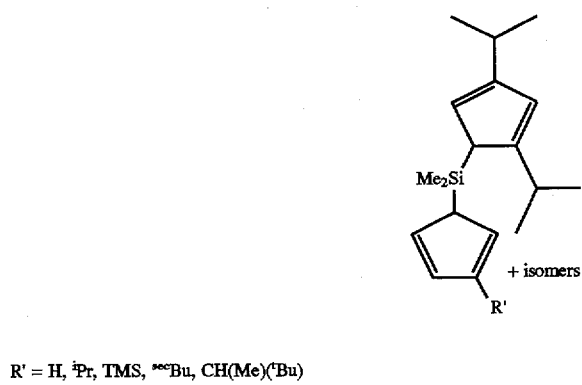

R' = H, iPr, TMS, secBu, CH(Me)(tBu)

Deprotonation of (iPr₂Cp)Me₂Si(R'Cp) with nBuLi in ether yields the singly bridged dianions, Li₂[(iPr₂Cp)Me₂Si (R'Cp)], as fine white solids. Reaction of Li₂[(iPr₂Cp)Me₂Si (R'Cp)] with Me₂SiCl₂ in tetrahydrofuran at −78° C. yields the doubly bridged ligands, (iPr₂Cp)(μ-Me₂Si)₂ (R'Cp) as shown below.

Synthesis of doubly bridged ligands, R'Thp (3–7).

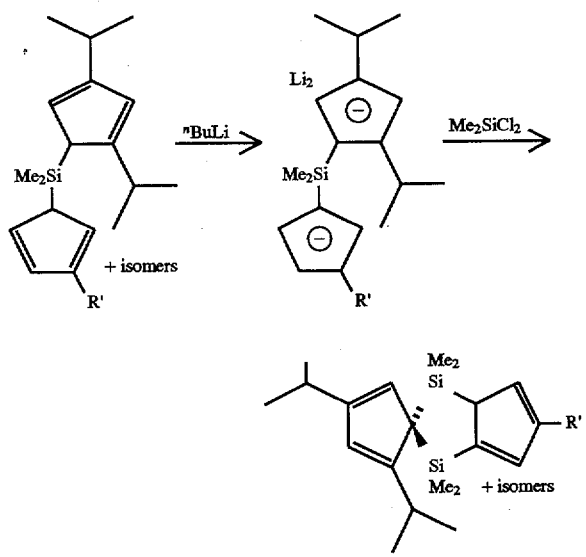

R' = H, iPr, TMS, secBu, CH(Me)(tBu)

The doubly bridged ligands are kugel-rohr distilled at high vacuum and 90–130° C. The overall yields of these reactions are typically in excess of 50% overall based on iPr₂Cp. These ligands have been given the trivial names R'Thp as shown below.

Trivial names for ligand 3–7

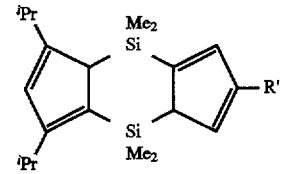

| | R' | ligand name |
|---|---|---|
| 3 | —H | Thp |
| 4 | —CHMe₂ | iPrThp |
| 5 | —SiMe₃ | TMSThp |
| 6 | —CH(Me)(Et) | sBuThp |
| 7 | —CH(Me)(tBu) | MNThp |

These R'Thp ligands can be deprotonated with either LiCH₂(SiMe₃) nBuLi or KOtBu to yield the C$_S$-symmetric dianionic ligands for Thp and TMSThp and C₁-symmetric dianionic ligands for sBuThp and MNThp.

Deprotonation of R'Thp (3, 5, 6, and 7).

R' = H, SiMe₃, CH(Me)(Et), CH(Me)(tBu)

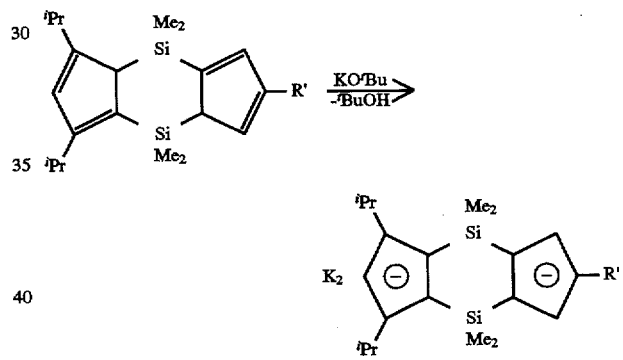

The only exception among the 5 different ligands presented above is the deprotonation of iPrThp. Reaction of iPrThp with either LiCH₂SiMe₃ or KOtBu yields a mixture of the C$_S$-symmetric 1,2,4 and the C₁-symmetric 1,2,3 isomers shown below.

Deprotonation of iPrThp (4).

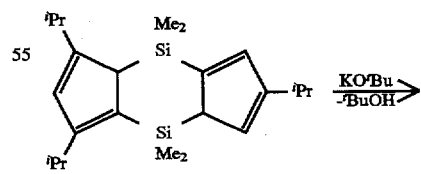

-continued

Deprotonation of $^iPrThp$ (4).

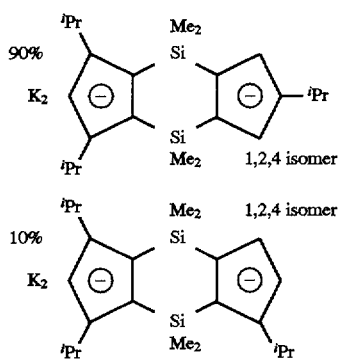

Fortunately, this problem with $^iPrThp$ deprotonation was solved by a one step deprotonation and metallation. Metallation of all of these ligands is carried out using an amine elimination route in which the protonated R'Thp ligands are treated with $Zr(NMe_2)_4$ in refluxing xylenes with a strong argon purge. The strong purge is necessary to remove dimethylamine gas from the reaction as it forms and thus drives the reaction to completion. Reaction of R'Thp, including $^iPrThp$, with $Zr(NMe_2)_4$ yields exclusively the 1,2,4 isomer of $R'ThpZr(NMe_2)_2$.

Metallation of R'Thp (3–7) to form 3A–7A.

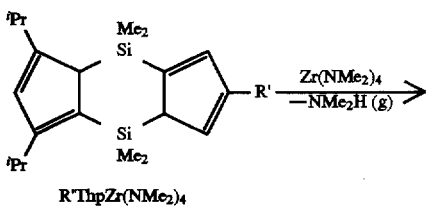

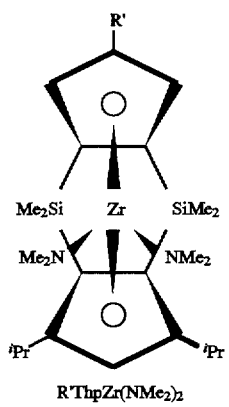

R' = H (3A), $^iPr$ (4A), $SiMe_3$ (5A), CH(Me)(Et) (6A), CH(Me)($^tBu$) (7A)

Reaction of $R'ThpZr(NMe_2)_2$ with excess trimethylsilyl-chloride in toluene results in rapid formation of $Me_3Si(NMe_2)$ and $R'ThpZrCl_2$.

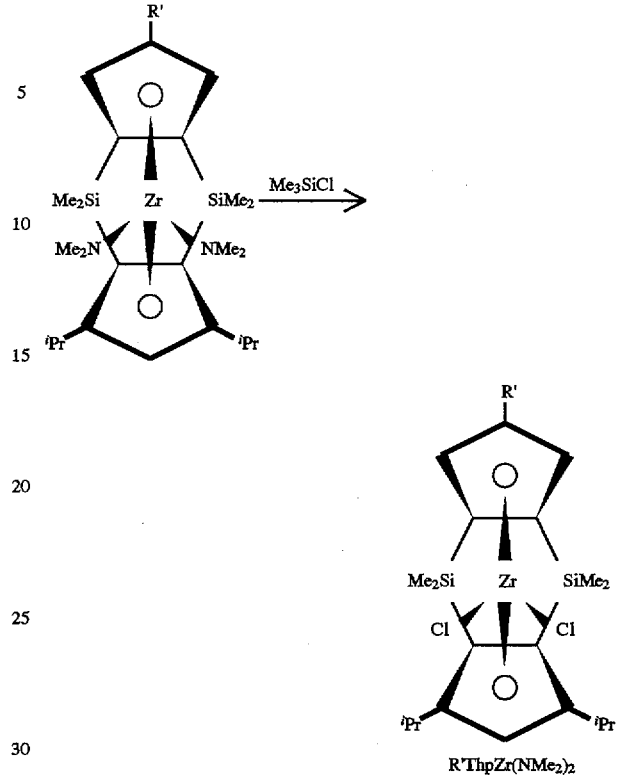

R' = H (3B), $^iPr$ (4B), $SiMe_3$ (5B), CH(Me)(Et) (6B), CH(Me)($^tBu$) (7B)

This synthetic scheme has proven to be an effective means of producing a variety of $C_S$- and $C_1$-symmetric complexes.

Polymerization

This new catalyst system may be employed in solution or supported in a solution, gas phase, high pressure, or bulk monomer polymerization process. The preferred processes are using bulk monomer and gas phase polymerization processes. Activator systems may be alkylaluminoxanes or ionic activators. The preferred activator is methylaluminoxane or ionic activators containing boron.

The resulting polymer produced by the catalyst system will preferably be a syndiotactic polyolefin. Most preferably the polyolefin is crystalline and syndiotactic. In a further embodiment two or more monomers are copolymerized to produce a copolymer. Mixtures of two or more metallocenes may be used to produce a blend of polymers. The polymers and copolymers produced according to this invention may be blended with commercial polyolefins.

To explore the reactivity of these new catalysts and to determine the effect of substitutions at R' on stereospecificity, a number of polymerizations were run. The 16 e-zirconium catalysts, $R'ThpZrCl_2$ (3B–7B), when activated by methylaluminoxane (MAO), initiate rapid polymerization of α-olefins to form polyolefins. The presumed initiating species for this type of reaction is a 14 e-, $d^0$ cationic metal alkyl as shown below.

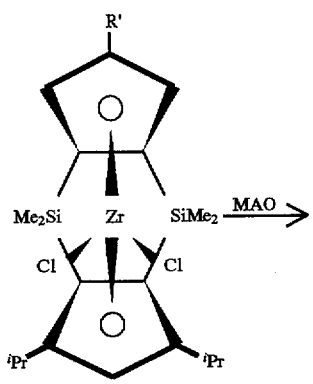

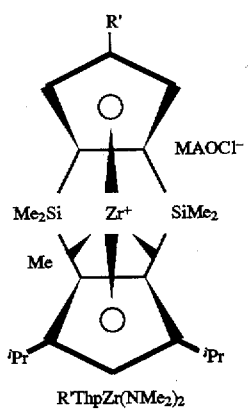

R'ThpZr(NMe₂)₂

R' = H, $^i$Pr, SiMe₃, CH(Me)(Et), CH(Me)($^t$Bu)

A table of propylene polymerization data is included below:

Polymerization data for catalysts 3B–7B.

| Entry | Cat[a] | R' | T °C. | [=/][c] | activity[d] | [r⁴][e] | [m⁴][e] | [r][f] | [m][g] |
|---|---|---|---|---|---|---|---|---|---|
| 3a | 3B | H | 0° | neat | 2160 | 83.7 | 0.0 | 94.0 | 6.0 |
| 3b | (C$_S$)[b] | H | 25° | 40 psig | 300 | 27.3 | ~0 | 74.1 | 25.9 |
| 3c | | H | 60° | neat | 74,200 | 76.0 | 0.1 | 92.6 | 12.6 |
| 4a | 4B | iPr | 0° | neat | 1750 | 98.9 | 0 | 99.6 | 0.4 |
| 4b | (C$_S$)[b] | IPr | 25° | 40 psig | 230 | 38.8 | ~0 | 75.6 | 24.3 |

-continued

Polymerization data for catalysts 3B–7B.

| Entry | Cat[a] | R' | T °C. | [=/][c] | activity[d] | [r⁴][e] | [m⁴][e] | [r][f] | [m][g] |
|---|---|---|---|---|---|---|---|---|---|
| 5a | 5B | TMS | 0° | neat | 1730 | 95.9 | 0 | 99.0 | 1.0 |
| 5b | (C$_S$)[b] | TMS | 25° | 40 psig | 230 | 33.9 | ~0 | 75.2 | 24.8 |
| 6a | 6B | $^S$Bu | 0° | neat | 1500 | 83.1 | 0.0 | 94.4 | 5.6 |
| 6b | (C$_1$)[b] | $^S$Bu | 25° | 40 psig | 200 | 20.0 | 4.8 | 62.0 | 38.0 |
| 7a | 7B | MN | 0° | neat | 930 | 41.8 | 5.6 | 73.5 | 26.5 |
| 7b | (C$_1$)[b] | MN | 25° | 40 psig | 156 | 0 | 61.2 | 14.6 | 85.4 |
| 7d | | MN | 25° | 10 psig | 110 | 0 | 58.5 | 17.6 | 82.4 |

[a]2 mg of catalyst in 0.5 ml toluene were added to a propylene/toluene/MAO suspension containing 500 mgs MAO (Albemarle).
[b]Symmetry of catalyst.
[c]Except for those in neat propylene (50 ml), samples were run in toluene (35 Ml).
[d]Grams of polymer isolated/g catalyst/hour (activity numbers are approximate at best).
[e]% of [rrrr] and [mmmm] pentad by $^{13}$C NMR (Complete data in table below).
[f][r] = [rr] + .5[mr].
[g][m] = [mm] + .5[mr].

Run 3c was performed under more industrially relevant conditions by Terry Burkhardt at the Exxon Chemical Company in Baytown, Tex. The properties of the resulting polymer were measured in comparison to the prototypical ($^i$PrFlCp)ZrCl₂/MAO catalyst system and are shown in the table below.

Comparison of polypropylene 3c (from ThpZrCl₂.(3B)/MAO) with polypropylene from ($^i$PrFlCp)ZrCl₂/MAO.

| catalyst | ThpZrCl₂ | ($^i$PrFLCp)ZrCl₂ |
|---|---|---|
| melting point | 131.2° C. | 138° C. |
| M$_w$ | 109,200 | 88,000 |
| PDI | 3.1 | 1.9 |
| [rr] | 87.5% | 88.2% |
| activity (g/g/hr.) | 74,200 | 30,300 |
| polymerization temp | ~60° C. | 60° C. |

C$_S$-symmetric catalysts: ThpZrCl₂ (3B), $^i$PrThpZrCl₂ (4B), and TMSThpZrCl₂ (5B), activated by MAO, all react with neat propylene at 0° C. to form highly syndiotactic polypropylene as shown in the table below in entries 3a, 4a, and 5a.

$^{13}$C NMR data for polymers 3a–7d.

| Entry | R' | mmmm (%) | mmmr | rmmr | mmrr | mmrm rrmr | rmrm | rrr | mrrr | mrrm |
|---|---|---|---|---|---|---|---|---|---|---|
| 3a | H | 0.0 | 0.0 | 1.7 | 4.0 | 3.0 | 1.6 | 83.7 | 6.0 | 0.0 |
| 3b | H | 0.0 | 2.0 | 3.7 | 6.9 | 21.8 | 11.6 | 27.3 | 19.1 | 7.5 |
| 3c | H | 0.1 | 0.4 | 1.7 | 3.4 | 6.0 | 1.0 | 76.0 | 10.3 | 1.1 |
| 4a | iPr | 0.0 | 0.0 | 0.1 | 0.3 | 0.5 | 0.0 | 98.9 | 0.3 | 0.0 |
| 4b | iPr | 0.0 | 3.6 | 4.1 | 7.6 | 21.7 | 3.9 | 38.8 | 17.6 | 2.6 |
| 5a | TMS | 0.0 | 0.0 | 0.0 | 0.0 | 2.0 | 0.0 | 95.9 | 2.2 | 0.0 |
| 5b | TMS | 0.0 | 3.1 | 3.8 | 6.6 | 22.7 | 6.4 | 33.9 | 19.9 | 3.6 |
| 6a | $^S$Bu | 0.0 | 0.4 | 1.5 | 3.0 | 4.6 | 0.0 | 83.1 | 7.5 | 0.0 |
| 6b | $^S$Bu | 4.8 | 8.2 | 5.1 | 12.3 | 20.4 | 7.1 | 20.01 | 15.6 | 6.5 |
| 7a | MN | 5.6 | 6.8 | 3.7 | 13.9 | 6.6 | 0.37 | 41.8 | 17.0 | 4.3 |
| 7b | MN | 61.2 | 15.5 | 0.0 | 14.3 | 2.9 | 0.0 | 0.3 | 0.4 | 5.3 |
| 7d | MN | 58.5 | 14.8 | 0.0 | 14.4 | 4.0 | 0.0 | 0.2 | 0.5 | 6.2 |

The polymer is obtained as a white powder, but it can be melted and cooled to obtain a hard transparent material.

The activity of these catalysts decreases as the size of R' increases, but it is only a modest decrease from 2160 g pol/g cat/hr for ThpZrCl$_2$ (3B) to 1730 g pol/g cat/hr for TMSThpZrCl$_2$ (5B). In addition to the slight decrease in activity, the syndioselectivity of the catalysts is clearly a function of the R' group. Of the C$_S$-symmetric catalysts, the syndiospecificity is highest for $^i$PrThpZrCl$_2$ (4B) and the lowest for ThpZrCl$_2$ (3B) as shown below. $^s$BuThpZrCl$_2$ is also included for comparison.

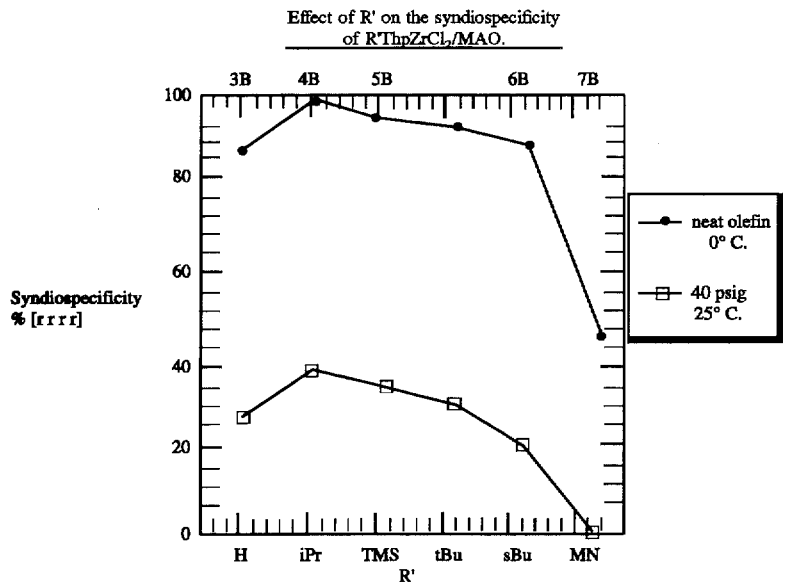

This study also shows that the syndioselectivity of the C$_S$-symmetric catalysts (R'=H, $^i$Pr, TMS, and $^s$Bu) is dependent on the concentration of olefin.

Dependence of Microstructure on Reaction Conditions

Using the MNThpZrCl$_2$ catalyst it has been observed that the microstructure of the polymer produced depends on the concentration of the reacting monomer. For example, when neat propylene is used at 0° C. the reaction produces syndiotactic polypropylene. In contrast, if the reaction is run using low propylene concentration the reaction produces isotactic polypropylene.

These reactions demonstrate that the catalysts of the present invention may be used to produce polymers with different microstructures by varying the reaction conditions in a simple way.

Experimental Procedures

General Considerations. All air or moisture sensitive chemistry was performed using standard high vacuum line, Schlenk, or drybox techniques under a nitrogen or argon atmosphere. All gases were purified with MnO on vermiculite and activated molecular sieves. Solvents were stored in vacuum transfer flasks over titanocene or sodium benzophenone ketyl. All other reagents were purified using standard methods. Unless otherwise mentioned, all chemicals were purchased from Aldrich and used as received. 6,6-dimethylfulvene is prepared by the method of Little. LAH is purified by ether extraction. Propylene is dried by passage through a Matheson 6110 drying system equipped with an OXISORB™ column. MAO (methylaluminoxane, Albemarle) was prepared by removing toluene in vacuo. The white MAO solid was dried at 25° C. for 48 hours at high vacuum. Dicyclopentadiene was thermally cracked and the distilled cyclopentadiene was stored at –60° C. Alkylchlorosilanes were distilled from CaH$_2$ immediately prior to use. YCl$_3$.3.5THF was prepared using a procedure identical to that reported by Manzer for the corresponding scandium complex. LiCH(SiMe$_3$)$_2$ was prepared by the method of Cowley. Fluorene and potassiumhexamethyldisilazide (KN (TMS)$_2$) were sublimed before use. 1,3-di-tert-butylcyclopentadiene was prepared by the method of Casserly.50

Instrumentation. NMR Spectra were recorded on a Bruker AM500 ($^1$H, 500.13 MHZ; $^{13}$C, 124.99 MHz) spectrometer, a Joel GX-400 ($^1$H, 399.7 MH Z) spectrometer, and a G.E. QE300 (1H, 300.1 MHz) spectrometer.

Li[$^t$Bu$_2$Cp)][DME]: A 500 ml flask is charged with di-tert-butylcyclopentadiene (6.4 g, 35.5 mmol) and pentane (200 ml), attached to a swivel frit assembly, and cooled to –78° C. n-BuLi (24 ml, 1.6M in hexanes, 39 mmol) is added via syringe and the reaction is warmed to 25° C. and stirred for 4 hours. DME (5 ml, 48 mmol) is added via syringe resulting in rapid gas evolution and precipitation of a white solid. The suspension is stirred for an additional hour and the solid is isolated on the frit and washed with pentane (3×200 ml) and dried at high vacuum for 2 hours; 7.116 g (73%).

($^t$Bu$_2$Cp)Me$_2$SiCl: A 200 ml flask is charged with Li($^t$Bu$_2$Cp)[DME] (4.80 g, 17.5 mmol) and tetrahydrofuran (70 ml), attached to a swivel frit assembly, and cooled to –78° C. Dichlorodimethylsilane (4.26 ml, 35 mmol) is vacuum transferred onto the reaction and the reaction is allowed to warm slowly to 25° C. without the aid of a water bath. After 9 hours of stirring at 25° C., all volatiles are removed in vacuo and the product is extracted with petroleum ether (3×20 mls). The solvent is removed in vacuo leaving a pale yellow oil; 4.47 g (94%).

Li$_2$[($^t$Bu$_2$Cp)Me$_2$Si(MeCp)][DME]: A 25 ml schlenk flask is charged with (tBu$_2$Cp)Me$_2$SiCl (2.0 g, 7.4 mmol) and tetrahydrofuran (15 Ml). A suspension of Li(MeCp) (680 mg, 7.9 mmol) in tetrahydrofuran (5 ml) is added via pipette to the stirred solution in the glove box. The clear colorless solution is stirred for 3 hours and solvent is removed in vacuo leaving a white paste. The product is extracted with petroleum ether (2×15 ml) using a cannula filter and the solvent is removed in vacuo leaving a yellow oil. The oil is dissolved in pentane (30 ml) and n-BuLi (9.3 ml, 1.6M in hexanes, 14.8 mmol) is added via syringe. The solution is stirred for 24 hours with no solid formation. DME (1.6 ml, 15.3 mmol) is added to the solution resulting in precipitate formation. The white suspension is stirred for an additional 2 hours and the solid is isolated on a frit. The white solid is washed with petroleum ether (2×10 ml) and dried at high vacuum for 2 hours; 2.25 g (60%).

$Li_2[(^tBu_2Cp)Me_2Si(^tBuCp)](THF)_n$ is prepared analogously by reaction of $(^tBu_2Cp)Me_2SiCl$ (2.47 g, 9.23 mmol) and $Li(^tBuCp)$ (1.18 g, 9.2 mmol) in tetrahydrofuran (20 ml) for 6 hours at 25° C. Deprotonation is carried out by reaction of the yellow oil in tetrahydrofuran (20 ml) with n-BuLi (11.5 ml, 1.6M in hexanes, 18.4 mmol). The reaction is stirred for 12 hours and the volatiles are removed in vacuo leaving an oily solid. Petroleum ether (20 ml) is added and the solid is stirred resulting in a white solid in a yellow solution. The solid is isolated on a frit, washed with petroleum ether (2×20 ml), and dried at high vacuum for 2 hours; 1.78 @(~40%).

3-isopropyl-6,6-dimethylfulvene. Isopropylcyclopentadiene (59.6 g, 0.555 mole), methanol (400 ml), acetone (35 g, 0.603 mole), and pyrrolidine (62 ml, 0.70 mole) were combined in a 1 L flask and stirred in air for 12 hr at 25° C. The solution is neutralized with glacial acetic acid. Water (600 ml) is added and the product is extracted with ether (4×400 ml) The organic layer is washed with water (4×600 ml) and dried over $MgSO_4$. The solvent is removed in vacuo. The yellow oil is kugel-röhr distilled at 90° C. and 50 torr yielding a bright yellow oil; 48.3 g (59%).

6,6-ethyl,methyl-fulvene was prepared analogously by reaction of cyclopentadiene (29.0 g, 438 mmol), 2-butanone (31.6 g, 438 mmole), and pyrrolidine (5 ml, 56 mmole) in methanol (200 ml). The yellow oil is kugel-röhr distilled at 90° C. and 50 torr yielding a bright yellow oil; 42.6 g (94%).

6,-tert-butyl-fulvene was prepared analogously by reaction of cyclopentadiene (31.7 g, 480 mmole), pivaldehyde (19.825 g, 230 mmole), and pyrrolidine (25 ml, 300 mmole) in methanol (250 ml). The yellow oil is kugel-röhr distilled at 70° C. and <1 torr yielding a bright yellow oil; 20.5 g (66.4%).

isopropylcyclopentadiene "$^iPrCp$." A solution of 6,6-dimethylfulvene (70.5 g, 0.663 mole) in anhydrous ether (200 ml) is slowly added via addition funnel to a well stirred 25° C. solution of LAH (0.670 mole) in ether (1 L) in a 3 L flask equipped with air driven overhead stirrer, efficient reflux condenser filled with dry ice/acetone, and $N_2$ adapter. The addition requires 1 hr. The reaction mixture is stirred for 4 more hours. The reaction mixture is quenched by addition of water (30 ml) via a syringe pump at a rate of 0.4 ml/min. CAUTION: Reaction is exothermic and produces large amounts of $H_2$ (g)!. NaOH (30 ml, 15% aqueous solution) is then added at a rate of 0.4 ml/min. and serves to form a pale yellow solution with a granular white solid. After $H_2$ evolution stops, water (1 L) is added to the reaction mixture. The product is extracted with ether (2×500 ml), the organic layer is washed with water (3×1 L), and the ether solution is dried with $MgSO_4$. The solvent is removed in vacuo and the product is distilled at 80° C. and −40 torr yielding a pale yellow oil; 65 g (90%).

sec-butyl-cyclopentadiene "sBuCp" ($C_5H_5CH(CH_3)(CH_2CH_3)$). A solution of 6,6-ethyl,methyl-fulvene (40 g, 333 mmol) in diethyl ether (300 ml) is slowly added via addition funnel to a well stirred 25° C. solution of LAH (553 mmol) in diethyl ether (1 L) in a 3 L flask equipped with air driven overhead stirrer, efficient reflux condenser filled with dry ice/acetone, and $N_2$ adapter. The addition requires 1 hr. The reaction mixture is stirred for 4 more hours. The reaction mixture is quenched by addition of water (20 ml) via a syringe pump at a rate of 0.4 ml/min. CAUTION: Reaction is exothermic and produces large amounts of $H_2$ (g)! NaOH (20 ml, 15% aqueous solution) is then added at a rate of 0.4 ml/min. and serves to form a pale yellow solution with a granular white solid. After $H_2$ evolution is complete, $H_2O$ (300 ml) is added slowly and the ether layer is separated. The reaction mixture is extracted with ether (300 ml) and the organic layers are combined and washed with $H_2O$ (3×200 ml). The yellow ether solution is dried over $MgSO_4$ and the solvent is removed in vacuo. The yellow liquid is kugel-röhr distilled at 100° C. and 20 torr; 25.39 g (62%).

1,3-diisopropylcyclopentadiene+isomers "$^iPr_2Cp$." A solution of 3-isopropyl-6,6-dimethylfulvene (48 g, 0.323 mole) in anhydrous ether (300 ml) is slowly added via addition funnel to a well stirred 25° C. solution of LAH (0.372 mole) in ether (700 ml) in a 3 L flask equipped with air driven overhead stirrer, efficient reflux condenser, and N2 adapter. The addition requires 1 hr. The reaction mixture is stirred for 4 more hours. The reaction mixture is quenched by addition of water (20 ml) at a rate of 1 ml/min. CAUTION: Reaction is exothermic and produces large amounts of $H_2$ (g)! NaOH (30 ml, 15% aqueous solution) is then added at a rate of 0.4 ml/min. and serves to form a pale yellow solution with a granular white solid. After $H_2$ evolution stops, water (1 L) is added to the reaction mixture. The product is extracted with ether (2×500 ml), the organic layer is washed with water (3×1 L), and the ether solution is dried with $MgSO_4$. The solvent is removed in vacuo and the product is distilled at 80° C. and −15 torr yielding a pale yellow oil; 38 g (78%).

lithium(isopropylcyclopentadienylide) "$Li(^iPrCp)$." A 1 L schlenk flask is charged with $^iPrCp$ (16.5 g, 153 mmol) and diethyl ether (700 ml). The flask is equipped with a 200 ml addition funnel which is charged with n-BuLi (100 ml, 1.6M in hexanes, 160 mmol). The n-BuLi is added to the ether solution slowly over 1 hour at 25° C. and white solid precipitates upon addition. The white suspension is stirred for 3 hours at 25° C. and the solid is filtered in the glove box and washed with diethyl ether (2×300 ml). The fine white solid is dried at high vacuum for 8 hours; 13.1 g (75%).

lithium(sec-butylcyclopentadienylide) "$Li(^sBuCp)$" is prepared analogously by reaction of 6,6-ethyl,methyl-fulvene (25.39 g, 207.7 mmol) and nBuLi (135 ml, 1.6M in hexanes, 216 mmol) in diethyl ether (1 L) in a 2 L schlenk flask. The white solid is dried at high vacuum and 50'° C. for 6 hours; 24 g (89.5%).

lithium(methylneopentyl-cyclopentadienylide) "Li (MNCp)." A 200 ml Schlenk flask is charged with 6,6-ethyl,methyl-fulvene (5.08 g, 37.8 mmol) and diethyl ether (150 ml). The yellow solution is cooled to 0° C. and MeLi (27 ml, 1.4M in diethylether, 37.8 mmol) is added via syringe over 15 minutes. A white solid precipitates during addition. The white suspension is warmed to 25° C. and stirred for 2 hours. The solid is filtered, washed with petroleum ether (4×100 ml), and dried at high vacuum for 5 hours; 5.21 g (88%).

lithium-1,3-diisopropylcyclopentadienylide "$Li(^iPr_2Cp)$" Toluene (200 ml) and petroleum ether (150 ml) are cannula transferred onto $^iPr_2Cp$ (24 g, 0.16 mole) in a large swivel frit assembly under argon. "BuLi (100 ml, 1.6M in hexanes, 0.16 mole) is added via cannula over a period of 30 minutes at 25° C. The solution is stirred overnight and the resulting white solid is filtered and washed with petroleum ether (4×100 ml). The white solid is dried in vacuo resulting in a fine white powder; 22.4 g (90%).

1-chloro-(3,5-diisopropylcyclopentadienyl-1,1-dimethylsilane "($^i$Pr$_2$Cp)Me$_2$SiCl." Tetrahydrofuran (150 ml) is vacuum transferred onto Li($^i$Pr$_2$Cp) (8.03 g, 51.4 mmol) in a medium swivel frit assembly at –78° C. with vigorous stirring. Dichlorodimethylsilane (9.57 g, 74.2 mmol) is then vacuum transferred onto the –78° C. solution and the reaction mixture is allowed to warm slowly to room temperature in a dry ice/acetone bath over 12 hours. The reaction is stirred at 25° C. for an additional 24 hours and then the volatiles are removed in vacuo leaving a white paste. The product is extracted away from the lithium chloride with petroleum ether (3×100 ml). The solvent is removed in vacuo resulting in a yellow oil; 11–85 g (95%).

1-cyclopentadienyl-1-(3,5-diisopropylcyclopentadienyl)-1,1-dimethylsilane "($^i$Pr$_2$Cp)Me$_2$Si(Cp)."

A suspension of sodiumcyclopentadienylide (4.05 g, 46 mmol) in tetrahydrofuran (50 ml) is added slowly to a solution of ($^i$Pr$_2$Cp)Me$_2$SiCl (9.06 g, 37.3 mmol) in tetrahydrofuran (100 ml). The reaction is stirred at 25° C. for 12 hours. The solvent is removed in vacuo and the product is extracted from the white sodium chloride with pentane (3×100 ml). The solvent is removed in vacuo leaving a pale yellow oil which is kugel-röhr distilled at 90° C. and <10–3 torr yielding a colorless oil; 8.22 g (81%).

1-(isopropyl-cyclopentadienyl)-1-(3,5-diisopropylcyclopentadienyl)-1,1-dimethylsilane "($^i$Pr$_2$Cp)Me$_2$Si($^i$PrCp)" is prepared analogously by reaction of ($^i$Pr$_2$Cp)Me$_2$SiCl (5.843 g, 51.202 mmol) and Li($^i$PrCp) (12.286 g, 50.514 mmol). The pale yellow oil is kugel-röhr distilled at 100° C. and <10–3 torr yielding a colorless oil; 13.899 g (87.5%).

1-(sec-butyl-cyclopentadienyl)-1-(3,5-diisopropylcyclopentadienyl)-1,1-dimethylsilane "($^i$Pr$_2$Cp)Me$_2$Si($^s$BuCp)" is prepared analogously by reaction of ($^i$Pr$_2$Cp)Me$_2$SiCl (17.512 g, 71.22 mmol) and Li($^s$BuCp) (9.452 g, 73.18 mmol). The pale yellow oil is kugel-röhr distilled at 100° C. and <10–3 torr yielding a pale yellow oil; 20.77 g (88.7%).

1-(methylneopentyl-cyclopentadienyl)-1-(3,5-diisopropylcyclopentadienyl)-1,1-dimethylsilane "($^i$Pr$_2$Cp)Me$_2$Si(MNCp)" is prepared analogously by reaction of ($^i$Pr$_2$Cp)Me$_2$SiCl (7.033 g, 28.96 mmol) and Li(MNCp) (4.70 g, 30.1 mmol). The pale yellow oil is kugel-röhr distilled at 110° C. and <10–3 torr yielding a pale yellow oil; 8.15 g (79%).

dilithio-1-cyclopentadienylide-1-(3,5-diisopropylcyclopentadienylide)-1,1-dimethylsilane, "Li$_2$[($^i$Pr$_2$Cp)Me$_2$Si(Cp)]." Toluene (100 ml) and petroleum ether (150 ml) are cannula transferred onto ($^i$Pr$_2$Cp)Me$_2$Si(Cp) (8.22 g, 30.2 mmol) in a medium porosity swivel frit assembly. nBuLi (39 ml, 1.6M in hexanes, 62.4 mmol) is added slowly, via syringe over 30 minutes at 25° C. and a white precipitate forms during addition. The reaction is stirred at 25° C. for 18 hours. The white solid is filtered and washed with petroleum ether (3×100 ml). The solid is dried in vacuo for 3 hours resulting in a fine white solid; 8.018 g (93%).

dilithio-1-(3-isopropyl-cyclopentadienyl)-1-(3,5-diisopropylcyclopentadienylide)-1,1-dimethylsilane "Li$_2$[($^i$Pr$_2$CP)Me$_2$Si($^i$PrCp)]." Diethyl ether (30 ml) is cannula transferred onto ($^i$Pr$_2$Cp)Me$_2$Si($^i$PrCp) (3.066 g, 9.746 mmol) in a 50 ml schlenk flask equipped with a 50 ml addition funnel. The funnel is charged with 13 mls of nBuLi (13 ml, 1:6M in hexanes, 21 mmol) and the nBuLi solution is added over 10 minutes to the 25° C. ether solution. A white solid precipitates during addition. The white suspension is stirred at 25° C. for 6 hours and filtered in the glove box. The solid is washed with petroleum ether (2×25 mL) and dried in vacuo for 6 hours; 2.84 g, (89%).

dilithio-1-(3-sec-butyl-cyclopentadienylide)-1-(3,5-diisopropylcyclopentadienylide)-1,1-dimethylsilane, "Li$_2$[($^i$Pr$_2$Cp)Me$_2$Si($^s$BuCp)]" is prepared analogously by the reaction of ($^i$Pr$_2$Cp)Me$_2$Si($^s$BuCp) (19.824 g, 60.326 mmol) and nBuLi (81 ml, 1.6M in hexanes, 130 mmol) in diethyl ether (600 ml); 15.5 g, (75%).

dilithio-1-(3-methylneopentyl-cyclopentadienylide)-1-(3,5-diisopropylcyclopentadienylide)-1,1-dimethylsilane, "Li$_2$[($^i$Pr$_2$Cp)Me$_2$Si(MNCp)]" is prepared analogously by the reaction of ($^i$Pr$_2$Cp)Me$_2$Si(MNCp) (8.15 g, 22.85 mmol) and nBuLi (32 ml, 1.6M in hexanes, 51.2 mmol) in diethyl ether (600 ml); 15.5 g, (75%).

($^i$Pr$_2$Cp)(μ-Me$_2$Si)$_2$(Cp), (3) "ThpH$_2$." A 250 ml round bottom flask is charged with Li$_2$[($^i$Pr$_2$Cp)Me$_2$Si(Cp)] (4.99 g, 17.5 mmol) and tetrahydrofuran (250 ml). The flask is attached to a medium porosity swivel frit assembly and the solution is cooled to –78° C. in an acetone/dry ice bath and degassed. Dichlorodimethylsilane (2.265 g, 17.5 mmol) is vacuum transferred onto the well stirred solution and the reaction mixture is stirred for 16 hours at –78° C., The reaction is allowed to warm slowly to 25° C. in about 8 hours in a dry ice/acetone bath, and is then stirred for 16 hours at 25° C. Solvent is removed in vacuo and the product is extracted away from the lithium chloride with petroleum ether (2×50 ml). The solvent is removed in vacuo leaving a yellow oil which is kugel-röhr distilled at 90° C. and high vacuum yielding a pale yellow oil; 4.946 g (86%).

($^i$Pr$_2$Cp)(μ-Me$_2$Si)$_2$($^i$PrCp), (4) "$^i$PrThpH$_2$" is prepared analogously by reaction of Li$_2$[($^i$Pr$_2$Cp)Me$_2$Si($^i$PrCp)] (2.84 g, 8.70 mmol) with Me$_2$SiCl$_2$ (1.12 g, 8.70 mmol)in tetrahydrofuran (40 ml). The yellow oil is kugel-röhr distilled at 120° C. and high vacuum yielding a pale yellow oil which slowly crystallizes as a white solid; 3.038 g (94.2%).

($^i$Pr$_2$Cp)(μ-Me$_2$Si)$_2$($^s$BuCp), (6) "$^s$BuThpH$_2$" is prepared analogously by reaction of Li$_2$[($^i$Pr$_2$Cp)Me$_2$Si($^s$BuCp)] (9.036 g, 26.539 mmol) with Me$_2$SiCl$_2$ (3.425 g, 26.538 mmol) in tetrahydrofuran (150 ml). The yellow oil is kugel-röhr distilled at 130° C. and high vacuum yielding a pale yellow oil which slowly crystallizes as a white solid; 7.583 g (74.0%).

($^i$Pr$_2$Cp)(μ-Me$_2$Si)$_2$(MNCp), (7) "MNThpH$_2$" is prepared analogously by reaction of Li$_2$[($^i$Pr$_2$Cp)Me$_2$Si(MNCp)] (7.60 g, 20.6 mmol) with Me$_2$SiCl$_2$ (2.66 g, 20.6 mmol) in tetrahydrofuran (150 ml). The yellow oil is kugel-röhr distilled at 130° C. and high vacuum yielding a pale yellow oil which crystallizes as a white solid; 4.3 g (50.0%).

K$_2$[($^i$Pr$_2$Cp)(μ-Me$_2$Si)$_2$(Cp)]"K$_2$Thp." In the glovebox, a suspension of potassium-tert-butoxide (2.30 g, 20.49 mmol) in diethylether (30 ml) is added to a stirred solution of ThpH$_2$ (3.345 g, 10.178 mmol) in diethylether (100 ml). The resulting white suspension is stirred at 25° C. for 30 minutes. The solid is isolated on a medium frit, washed with diethylether (3×40 ml), and dried in vacuo for 2 hours resulting in a coarse white solid; 4–05 g (98%).

($^i$Pr$_2$Cp)(μ-Me$_2$Si)$_2$(TMSCp), (5) "TMSThpH$_2$." A 50 ml Schlenk flask is charged with K$_2$Thp (0.653 g, 1.613 mmol) and tetrahydrofuran (30 ml). The white suspension is cooled to –78° C. with stirring, trimethylsilylchloride (0.175 g, 1.615 mmol) is vacuum transferred into the schlenk flask, and the flask is warmed to 25° C. After 6 hours, the suspension has turned into a clear yellow solution. The solution is stirred an additional 6 hours, volatiles are removed in vacuo leaving a yellow foam, and diethyl ether (20 ml) is added to form a white suspension. With vigorous stirring, H$_2$O (20 ml) is added slowly and the mixture is transferred to a separatory funnel. The ether layer is separated and the aqueous layer is extracted with diethyl ether (2×20 ml). The organic layers are combined, washed with $H_2O$ (2×50 ml) and dried over $MgSO_4$. Solvent is removed in vacuo and the yellow oil is dried at high vacuum for 1 hour. The oil is kugel-rohr distilled at 130° C. and high vacuum yielding a white solid; 0.46 g (71%).

ThpZrCl$_2$ (3B) (Method 1) In the glovebox, ZrCl$_4$(THF)$_2$ (1.89 g, 5.01 mmol) is added to a suspension of K$_2$Thp (2.024 g, 5.0 mmol) in tetrahydrofuran (20 ml.) and the resulting suspension is stirred for 3 hours. The solvent is removed in vacuo and toluene (40 ml) is added to form a brown suspension. The suspension is filtered through a bed a Celite and the toluene soluble fraction is dried in vacuo leaving a yellow orange solid. The solid is washed with pentane (25 ml) and dried in vacuo resulting in a fine white solid; 980 mg (40%).

ThpZr(NMe$_2$)$_2$. (3A) A 100 ml schlenk flask is charged with ThpH$_2$ (3) (3.069 g, 9.338 mmol), xylenes (30 ml), and Zr(NMe$_2$)$_4$ (2.498 g, 9.338 mmol). The flask is equipped with a reflux condenser and a 180° Teflon needle valve. Under a strong argon purge the reaction is heated to reflux in a 160° C. oil bath. The reaction is monitored by holding a wet piece of pH paper up to the vent needle. The reaction is allowed to cool to 25° C. after no more NMe$_2$H is released and the pH paper gives a neutral reading. Total reaction time is typically 12 hours, but the reaction time depends on the strength of the Ar flow. The solvent is removed in vacuo and the yellow solid is dried at high vacuum for 12 hours. The solid is recrystallised from petroleum ether yielding yellow microcrystals; 3.5 g (several crops), (74%).

$^i$PrThpZr(NMe$_2$)$_2$ (4A) is prepared analogously with $^i$PrThp (4) (3.003 g, 8.100 mmol) and Zr(NMe$_2$)$_4$ (2.175 g, 8.130 mmol) in refluxing xylenes (20 ml) for 18 hours. The solid is dried at high vacuum yielding a yellow/orange solid which is not purified further; 4.40 g (98%).

TMSThpZr(NMe$_2$)$_2$ (5A) is prepared analogously with TMSThp (5) (379 mg, 0.945 mmol) and Zr(NMe$_2$)$_4$ (254 mg, 0.949 mmol) in refluxing xylenes (15 ml) for 14 hours. The solvent is removed in vacuo leaving an orange oil which is not purified further; 507 mg (93%)

$^t$BuThpZr(NMe$_2$)$_2$ (6A) is prepared analogously with $^t$BuThp (6) (2.02 g, 5.25 mmol) and Zr(NMe$_2$)$_4$ (1.41 g, 5.27 mmol) in refluxing xylenes (15 ml) for 15 hours. The solid is dried at high vacuum yielding a fine yellow solid which is not purified further; 2.9 g (98%).

MNThpZr(NMe$_2$)$_2$ (7A) is prepared analogously with MNThp (7) (4.3 g, 10.32 mmol) and Zr(NMe$_2$)$_4$ (2.76 g, 10.32 mmol) in refluxing xylenes (30 ml) for 28 hours. The solid is dried at high vacuum yielding a yellow/orange solid which is not purified further; 5.59 g (92%).

ThpZrCl$_2$ (3B) (Method 2) A 25 ml Schlenk flask is charged with 3A (0.714 g, 1.41 mmol) and toluene (10 ml). Excess trimethylsilylchloride (1.0 ml, 7.8 mmol) is syringe added to the solution at 25° C. The solution is stirred for an hour and the solvent is removed in vacuo yielding a pale yellow solid. Petroleum ether (5 ml) is added to the solid and the resulting yellow suspension is filtered and washed with cold petroleum ether (3×5 ml). The resulting white solid is dried at high vacuum for 2 hours; 450 mg (65.2%). Analysis: Calculated (Found) C: 49.15 (49.01); H: 6.91 (5.92).

$^i$PrThpZrCl$_2$ (4B). A 50 ml Schlenk flask is charged with 4A (4.40 g, 8.02 mmol) and toluene (20 ml). Trimethylsilylchloride (3.5 ml, 27 mmol) is syringe added to the solution at 25° C. After 5 minutes, a white solid begins to precipitate from the yellow solution. The suspension is stirred for an hour and the solvent is removed in vacuo yielding a yellow solid. Petroleum ether (20 ml) is added to the solid and the resulting yellow suspension is filtered and washed with petroleum ether (3×20 ml). The resulting white solid is dried at high vacuum for 2 hours; 2.65, g (62.2%). Analysis: Calculated (Found) C: 52.04 (52.10); H: 6.84 (7.14).

TMSThpZrCl$_2$ (5B) is prepared analogously with 5A (400 mg, 0.69 mmol) and trimethylsilylchloride (0.3 ml, 2.4 mmol) in toluene (10 ml); 296 mg (75%). Analysis: Calculated (Found) C: 49.25.(48.87); H: 6.83 (6.62).

$^t$BuThpZrCl$_2$ (6B) is prepared analogously with 6A (2.9 g, 5.16 mmol) and trimethylsilylchloride (3.0 ml, 23 mmol) in toluene (10 ml); 1.64 g (58.3%). Analysis: Calculated (Found) C: 52.91 (52.94); H: 7.03 (7.07).

MNThpZrCl$_2$ (7B) is prepared analogously with 7A (1.18 g, 2.00 mmol) and trimethylsilylchloride (1.5 ml, 12 mmol) in toluene (20 ml); 437 mg (38%). Analysis: Calculated (Found) C: 54.51 (54.46); H: 7.39 (7.54).

Polymerization Procedures: CAUTION: All of these procedures should be performed behind a blast shield. 2a, 3a, 4a, 5a, 7a (neat olefin, 0° C.). A 100 ml high pressure glass reactor equipped with a septa port, large stir bar, and pressure gauge (0–200 psig) is charged with MAO (500 mg, 8.6 mmol). The reactor is connected: to a propylene line (120 psig) and the reactor is purged with propylene for approximately 2 minutes at 120 psig. The reactor is placed in a 0° C. ice water bath and propylene (~50 ml, ~1.2 mol) is condensed in the reactor. The propylene inlet valve is then shut and a solution containing catalyst (3B, 4B, 5B, 7B) (~2 mg, ~0.004 mmol) in toluene (0.5 ml) is added to the vigorously stirred MAO/propylene suspension via a 1 ml gas tight syringe through the septa (The addition requires significant force since the pressure in the reactor is ~95 psig). The reaction is stirred for 10 minutes during which time polymer is observed to precipitate from the reaction mixture. At this point the reaction is quenched with MeOH (1 ml in a gas tight syringe) by slow addition while venting the propylene from the reactor. An additional 20 ml is added once the pressure in the reactor is below 2 atmospheres and the white suspension is stirred vigorously for 1 hour to ensure complete quenching of the MAO. The suspension is then added to a vigorously stirred HCl (100 ml of a 20% solution in MeOH). The suspension is stirred for 2 hours and is then filtered and washed with MeOH (4×50 ml). The resulting white powder is then dried at high vacuum for 4 hours.

6a is prepared analogously using catalyst 6B. After the reaction is complete, a white solid mass has formed in the bottom of the reactor. After quenching with MeOH as above. The polymer is removed from the reactor and is added to a vigorously stirred HCl (100 ml of a 20% solution in MeOH). The polymer is stirred in the solution for 2 hours and is then filtered and washed with MeOH (4×50 ml). The resulting polymer is a relatively soft material with some elasticity. The polymer is soxhlet extracted with refluxing toluene for 24 hours. The solvent is removed in vacuo and the solid is dried at high vacuum for 3 hours.

3b, 4b, 5b, 6b, (40 psig, toluene, 25° C.). A 100 ml high pressure glass reactor equipped with a septa port, large stir bar, and pressure gauge (0–200 psig) is charged with MAO (500 mg, 8.6 mmol), toluene (35 ml), and catalyst (3B–6B) (10 mg, ~0.02 mmol). Upon addition of catalyst to the MAO/toluene suspension, the color typically changes from white to pale yellow. The reactor is connected to a propylene line (40 psig) and the reactor is purged with propylene for 5 minutes at 40 psig and 25° C. The reactor vent is closed and the propylene pressure is maintained at 40 psig for an additional 25 minutes with vigorous stirring at 25° C. The propylene inlet is then shut and the reactor is vented to remove the excess propylene. Once the vent is opened, MeOH (10 ml) is added to the reaction mixture to quench the MAO. An additional 20 ml of MeOH are added once the propylene is gone. The suspension is stirred vigorously for two hours and then all volatiles are removed by rotary evaporation. The resulting polymer is then placed in a soxhlet thimble and the product is extracted from refluxing toluene over the course of 24 hours. The product is dried at high vacuum forming a tacky sticky solid.

7b is prepared analogously using catalyst 7B. However, upon quenching the reaction with MeOH, a fine white powder precipitates and the suspension is stirred vigorously for 1 hour. The suspension is then added to a vigorously stirred HCl solution (200 ml of a 20% solution in MeOH). The suspension is stirred for 2 hours and is then filtered and washed with MeOH (4×50 ml). The resulting white powder is then dried at high vacuum for 4 hours.

7d is prepared analogously using catalyst 7B, except that the propylene pressure is now maintained at 10 psig.

3c. In the glove box, a stainless steel high pressure bomb, equipped with a mechanical stirrer and pressure gauge, is charged with MAO (800 mg, 14 mmol). An ampoule containing ThpZrCl$_2$ (11 mg, 0.022 mmol) in toluene (0.5 ml) is attached to the stirrer such that it can be broken by rapid stirring. ~100 ml of propylene are condensed into the bomb and the propylene/MAO mixture is brought to 60° C. in an oil bath and allowed to equilibrate for 1 hour. At this point, the stirrer is started quickly, breaking the ampoule immediately. The reaction temperature increases as evidenced by a pressure increase to ~400 psig and after 20 minutes the mixture becomes so viscous as to stop the stirrer. The excess propylene is then vented and the reactor is opened. MeOH is added to quench the reaction and the product is scraped out of the reactor; 120 g.

| Compound | Assignments | δ(ppm) | $J_{C-H}$ |
|---|---|---|---|
| Li(tBu2Cp)[DME] | tBu(18H) | 1.53(s) | |
| THF-d8 | Cp—H(2H) | 5.88(s) | |
| | (1H) | 5.92(s) | |
| | DME(6H) | 2.81(s) | |
| | (4H) | 2.52(s) | |
| (tBu$_2$Cp)Me$_2$SiCl | (CH$_3$)$_2$SiCl(6H) | 0.218(s) | |
| | tBu(18H) | 1.20(s) | |
| | Cp—H(2H) | 7.1(s) | |
| | (1H) | 6.48(s) | |
| Li$_2$[(tBu$_2$Cp)Me$_2$Si— | (CH$_3$)$_2$SiCl(1H) | 0.42(s) | |
| (MeCp)][DME] | (CH$_3$)$_2$SiCl(6H) | 0.39(s) | |
| 2 isomers THF-d8 | tBu(1.3H),(13H) | 1.19(s),1.25(s) | |
| | tBu(9H),(9H) | 1.21(s),1.26(s) | |
| | Cp—Me(<1H) | 2.11(s) | |
| | Cp—Me(3H) | 2.09(s) | |
| | Cp—H(<1H) | 5.5–6.0 | |
| | Cp—H(5H) | 5.5–6.0 | |
| Li$_2$(tBu$_2$Cp)Me$_2$Si— | (CH$_3$)$_2$SiCl(6H) | 0.40(s) | |
| (tBuCp)](THF)$_n$ | tBu(9H) | 1.21(s) | |
| 1 Isomer THF-d8 | (9H) | 1.24(s) | |
| | (9H) | 1.27(s) | |
| | Cp—H(1H) | 5.71(t) | |
| | (1H) | 5.76(d) | |
| | (1H) | 5.78(t) | |
| | (1H) | 5.88(t) | |
| | (1H) | 5.96(d) | |
| 3-isopropyl-6,6- | (CH$_3$)$_2$CH(6H) | 1.18(d) | |
| dimethylfulvene | (CH$_3$)2CH(1H) | 2.70(h) | |
| CDCl$_3$ | (CH$_3$)$_2$C(6H) | 2.16(s) | |
| | Cp—H(1H) | 6.16(q) | |
| | (1H) | 6.45(q) | |
| | (1H) | 6.52(q) | |
| iPr$_2$Cp CDCl$_3$ | (CH$_3$)$_2$CH(12H) | 1.07(d),1.11(d), 1.70(d) | |
| | (CH$_3$)$_2$CH(2H) | 2.3–2.7(b) | |
| | Cp—H(4H) | 2.3–3.0, 5.98–6.05 | |
| Li(iPr$_2$Cp) THF-d8 | (CH$_3$)$_2$CH(12H) | 1.15(d) | 6.667 |
| | (CH$_3$)$_2$CH(2H) | 2.73(h) | 6.808 |
| | Cp—H(2H) | 5.33(d) | 2.447 |
| | (1H) | 5.37(t) | 2.442 |
| (iPr$_2$Cp)Me$_2$SiCl | (CH$_3$)$_2$CH(6H) | 0.051(b),0.23(b) | |
| | (CH$_3$)$_2$CH(12H) | 1.01(d),1.08(d), 1.11(d) | |
| | (CH$_3$)$_2$CH(2H) | 2.50(h),3.06(h) | |
| | Cp—H | 2.58(b),2.81(b), 3.39(b),6.26(s), 6.28(m) | |
| (iP4$_2$Cp)Me$_2$Si(Cp) | (CH$_3$)$_2$Si(6H) | −0.3–0.2 | |
| | (CH$_3$)$_2$CH(12H) | 1.0–1.3 | |
| | (CH$_3$)$_2$CH(~2H) | 2.5–3 | |
| | Cp—H(~8H) | 3.0–3.6,6.0–6.8 | |
| (iPr$_2$[(iPr$_2$Cp)(Me$_2$Si(Cp)] | (CH$_3$)$_2$Si(6H) | .334(s) | |

$^1$H and $^{13}$C NMR Data (in C$_6$D$_6$, unless otherwise mentioned)

$^1$H and $^{13}$C NMR Data (in $C_6D_6$, unless otherwise mentioned) -continued

| Compound | Assignments | δ(ppm) | $J_{C-H}$ |
|---|---|---|---|
| THF = d8 | $(CH_3)_2CH(6H)$ | 1.14(d) | |
| | (6H) | 1.16(d) | |
| | $(CH_3)_2CH(1H)$ | 2.76(h) | |
| | (1H) | 3.22(h) | |
| | Cp—H(2H) | 5.96(t) | |
| | (2H) | 5.80(t) | |
| | (1H) | 5.66(d) | |
| | (1H) | 5.62(d) | |
| ($^iPR_2Cp)(Me_2Si)_2(Cp)$ = | $(CH_3)_2Si(12H)$ | −1.0−0.6 | |
| "Thp"H2(3) | $(CH_3)_2CH(12H)$ | 1.0−1.3 | |
| | $(CH_3)_2CH(\sim 2H)$ | 2.5−3.3 | |
| | Cp—H(~6H) | 3.3−4.0, | |
| | | 6.4−7.0 | |
| $Li_2$(Thp) THF-d8 | $(CH_3)_2Si(3H)$ | −0.572(s) | |
| | (3H) | 0.206(s) | |
| | (3H) | 0.322(s) | |
| | (3H) | 0.444(s) | |
| | $(CH_3)_2CH(3H)$ | 1.11(s) | |
| | (3H) | 1.13(s) | |
| | (3H) | 1.15(s) | 6.809 |
| | (3H) | 1.25(s) | 6.346 |
| | $(CH_3)_2CH(1H)$ | 2.75(h) | 6.548 |
| | (1H) | 3.11(h) | 6.863 |
| | Cp—H(2H) | 6.008(s) | |
| | (1H) | 6.10(s) | |
| | (1H) | 6.356(s) | |
| $K_2$(Thp) THF-d8 | $(CH_3)_2Si(12H)$ | 0.368(s) | |
| | $(CH_3)_2CH(12H)$ | 1.23(d) | 6.60 |
| | $(CH_3)_2CH(2H)$ | 3.18(h) | 6.65 |
| | Cp—H(1H) | 5.973(s) | |
| | (3H) | 6.241(s) | |
| (Thp)Zr(NMe$_2$)$_2$ | $(CH_3)_2Si(6H)$ | .575(s) | |
| (3A) | (6H) | 0.748(s) | |
| | $(CH_3)_2CH(6H)$ | 1.096(d) | |
| | (6H) | 1.314(d) | |
| | $(CH3)_2CH(2H)$ | 3.0(m) | |
| | $Zr(N(CH_3)_2)_2(12H)$ | 2.91(s) | |
| | Cp—H(H)(1H) | 6.202(t) | |
| | (1H) | 6.280(s) | |
| | (2H) | 6.545(d) | |
| (Thp)ZrCl$_2$ (3B) $^1$H | $(CH_3)_2Si(6H)$ | 0.376(5) | |
| | (6H) | 0.546(5) | |
| | $(CH_3)_2CH(6H)$ | 0.926(d) | 7.16 Hz |
| | (6H) | 1.348(d) | 6.60 Hz |
| | $(CH3)_2CH(2H)$ | 2.905(h) | 6.85 Hz |
| | Cp—H(H)(1H) | 6.348(t) | |
| | (1H) | 6.452(5) | |
| | (2H) | 6.737(d) | |
| (Thp)ZrCl$_2$ (3B) $^{13}$C | $(CH_3)_2Si$ | −1.542 | |
| | | 3.502 | |
| | $(Ch_3)_2CH$ and | 20.895 | |
| | $(CH_3)_2CH$ | 28.645 | |
| | | 29.631 | |
| | | 110.190 | |
| | | 114.043 | |
| | Cp | 115.123 | |
| | | 116.378 | |
| | | 138.196 | |
| | | 165.097 | |
| ($iPr_2Cp)(Me_2Si)_2$— | $(CH_3)Si(21H)$ | −0.5−0.7 | |
| (TMSCp) = | $(CH_3)_2CH(12H)$ | 1.0−1.3 | |
| "TMSThp" | $(CH_3)_2CH(\sim 2H)$ | 2.5−3.5 | |
| (5) | Cp—H(~5H) | 3.0−3.5, 6.4−7.3 | |
| $K_2$(TMSThp) THF-d8 | $(CH_3)Si(_2 1H)$ | 0.15(s) | |
| | $(CH_3)_2CH(12H)$ | 1.15(d) | 6.766 |
| | $(CH_3)_2CH(2H)$ | 3.04(s) | 6.793 |
| | Cp—H(1H) | 5.79(s) | |
| | (2H) | 6.35(s) | |
| (TMSThp)Zr(NMe$_2$)$_2$ | $(CH_3)_3Si(9H)$ | 0.25(s) | |
| (5A) | $(CH_3)_2Si(6H)$ | 0.60(s) | |
| | (6H) | 0.69(s) | |
| | $(CH_3)_2CH(6H)$ | 1.17(d) | 6.859 |
| | (6H) | 1.32(d) | 6.697 |
| | $(CH_3)_2CH(2H)$ | 2.85(m) | 6.789 |
| | $Zr(N(CH_3)_2)_2(12H)$ | 2.71(s) | |
| | Cp—H(1H) | 6.40(s) | |

-continued

| Compound | Assignments | δ(ppm) | $J_{C-H}$ |
|---|---|---|---|
| | (2H) | 6.67(s) | |
| (TMSThp)ZrCl$_2$ (5B) | (CH$_3$)$_3$Si(9H) | 0.477(s) | |
| $^1$H | (CH$_3$)$_2$Si(6H) | 0.4811(s) | |
| | (6H) | 0.6176(s) | |
| | (CH$_3$)$_2$CH(6H) | 0.94(d) | |
| | (6H) | 1.32(d) | |
| | (CH$_3$)$_2$CH(2H) | 2.91(h) | |
| | Cp—H(1H) | 6.42(s) | |
| | (2H) | 6.98(s) | |
| (TMSThp)ZrCl$_2$ (5B) | (CH$_3$)$_3$Si and | −1.664 | |
| $^{13}$C | (CH$_3$)$_2$Si | 0.157 | |
| | | −3.381 | |
| | (CH$_3$)$_2$CH and | 20.681 | |
| | (CH$_3$)$_2$CH | 28.524 | |
| | | 29.618 | |
| | | 109.334 | |
| | | 114.340 | |
| | Cp | 119.557 | |
| | | 126.773 | |
| | | 143.185 | |
| | | 165.064 | |
| 6-tert-butylfulvene | (CH$_3$)CCH(9H) | 1.05(s) | |
| | (CH$_3$)CCH(1H) | 6.17(s) | |
| | Cp—H(1H) | 6.19(m) | |
| | (1H) | 6.395(m) | |
| | (1H) | 6.575(m) | |
| | (1H) | 6.69(m) | |
| Li[CpC(H)(CH$_3$)— | (CH$_3$)CC(CH$_3$)H(9H) | .8311(s) | |
| (CMe$_3$)] Li"MN" | (CH$_3$)CC(CH$_3$)H(3H) | 1.179(d) | 7.15 Hz |
| THF-d8 | (CH$_3$)CC(CH$_3$)H(1H) | 2.435(q) | 7.207 Hz |
| | Cp—H(4H) | 5.52(m),5.54(m) | |
| Li$_2$[(iPr$_2$Cp)Me$_2$Si— | (CH$_3$)$_2$Si(6H) | 0.3075(s) | |
| ($^i$PrCp)] THF-d8 | (CH$_3$)$_2$CH(6H) | 1.144(d) | 6.72 |
| | (6H) | 1.158(d) | 6.86 |
| | (6H) | 1.170(d) | 6.76 |
| | (CH$_3$)$_2$CH(1H) | 2.772(h) | 6.774 |
| | (1H) | 2.814(h) | 6.835 |
| | (1H) | 3.233(h) | 6.76 |
| | Cp—H(1H) | 5.6257(d | 2.24 |
| | (2H) | 5.69(m) | |
| | (2H) | 5.83(m) | |
| ($^i$Pr$_2$Cp)(Me$_2$Si)$_2$($^i$PrCp) = | (CH$_3$)$_2$Si(12H) | −0.336(s) | |
| "$^i$PrThp" (4) | | −0.239(s) | |
| | | 0.555(s) | |
| | | 0.603(s) | |
| | (CH$_3$)$_2$CH(18H) | 1.106(d) | 6.692 |
| | | 1.280(d) | 6.560 |
| | | 1.306(d) | 6.813 |
| | | 2.672(m) | 6.547 |
| | (CH$_3$)$_2$CH(3H) | 2.862(m) | 6.524 |
| | | 3.188(m) | 6.561 |
| | | 3.461(s) | |
| | | 3.558(s) | |
| | Cp—H(5H) | 6.50(s) | |
| | | 7.20(s) | |
| ($^i$PrThp)Zr(NMe$_2$)$_2$ | (CH$_3$)$_2$Si(6H) | 0.595(s) | |
| (4A) | (6H) | 0.720(s) | |
| | (CH$_3$)$_2$CH(6H) | 1.187(d) | 6.857 |
| | (6H) | 1.204(d) | 6.816 |
| | (6H) | 1.342(d) | 6.733 |
| | (CH$_3$)$_2$CH(3) | 2.8–2.95(m) | |
| | Zr(N(CH$_3$)$_2$)$_2$(12H) | 2.773(s) | |
| | Cp—H(1H) | 6.356(s) | |
| | (2H) | 6.387(s) | |
| ($^i$PrThp)ZrCl$_2$ (4B) $^1$H | (CH$_3$)$_2$Si(6H) | 0.461(s) | |
| | (6H) | 0.605(s) | |
| | (CH$_3$)$_2$CH(6H) | 0.951d) | 7.142 |
| | (6H) | 1.341(d) | ~6.167 |
| | (6H) | 1.357(d) | ~6.145 |
| | (CH$_3$)$_2$CH(2H) | 2.928(h) | 6.84 |
| | (1H) | 3.200(h) | 6.90 |
| | Cp—H(2H) | 6.466(s) | |
| | (1H) | 6.678(s) | |
| ($^i$PrThp)ZrCl$_2$ (4B) $^{13}$C | (CH$_3$)$_2$Si | −1.582 | |
| C$_6$D$_6$/THF | | 3.531 | |
| | (CH$_3$)$_2$CH and | 20.769 | |

-continued

$^1$H and $^{13}$C NMR Data (in $C_6D_6$, unless otherwise mentioned)

| Compound | Assignments | δ(ppm) | $J_{C-H}$ |
|---|---|---|---|
| | $(CH_3)_2CH$ | 23.761 | |
| | | 28.533 | |
| | | 28.585 | |
| | | 29.682 | |
| | | 110.229 | |
| | | 113.814 | |
| | Cp | 115.539 | |
| | | 135–801 | |
| | | 139.625 | |
| | | 164.848 | |
| $Li_2[(^iPr_2Cp)Me_2Si$ | $(CH_3)_2Si(6H)$ | 0.2965(s) | |
| (MNCp)] | $(CH_3)_3CH(CH_3)(9H)$ | 0.843(s) | |
| | $(CH_3)_3CH(CH_3)(3H)$ | 1.14(d) | |
| | $(CH_3)_2CH(6H)$ | 1.13(d) | |
| | (6H) | 1.17(d) | |
| | $(CH_3)_3CH(CH_3)(1H)$ | 2.46(q) | |
| | $(CH_3)_2CH(1H)$ | 2.770(h) | |
| | (1H) | 3.188(h) | |
| | Cp—H(2H) | 5.648(s) | |
| | (1H) | 5.664(s) | |
| | (1H) | 5.804(s) | |
| | (1H) | 5.831(s) | |
| $K_2(MNThp)$ | $(CH_3)_2Si(6H)$ | 0.3714(s) | |
| | (6H) | 0.3805(s) | |
| | $(CH_3)_3CH(CH_3)(9H)$ | 0.9266(s) | |
| | $(CH_3)_3CH(CH_3)(3H)$ | 1.197(d) | 7.117 |
| | $(CH_3)_2CH(12H)$ | 1.225(d) | 6.643 |
| | $(CH_3)_3CH(CH_3)(1H)$ | 2.581(q) | 7.214 |
| | $(CH_3)_2CH(2H)$ | 3.209(h) | 6.791 |
| | Cp—H(1H) | 5.973(s) | |
| | (2H) | 6.023(s) | |
| $(MNThp)Zr(NMe_2)_2$ | $(CH_3)_2Si(3H)$ | 0.5660(s) | |
| (7A) | (3H) | 0.6530(s) | |
| | (3H) | 0.6885(s) | |
| | (3H) | 0.6994(4) | |
| | $(CH_3)_3CH(CH_3)(9H)$ | 0.9118(s) | |
| | $(CH_3)_3CH(CH_3)(3H)$ | 1.202(d) | 6.800 |
| | $(CH_3)_2CH(3H)$ | 1.19(d) | 7.289 |
| | (3H) | 1.215(d) | 6.238 |
| | (3H) | 1.337(d) | 6.691 |
| | (3H) | 1.361(d) | 6.711 |
| | $Zr(N(CH_3)-)_2(6H)$ | 2.7056(s) | 7.199 |
| | (6H) | 2.8683(s) | |
| | $(CH_3)_3CH(CH_3)(1H)$ | 2.64(q) | |
| | $(CH_3)_2CH(2H)$ | 2.87–3.0(m) | |
| | Cp—H(1H) | 6.3609(s) | |
| | (1H) | 6.4093(s) | |
| | (1H) | 6.4333(s) | |
| $(MNThp)ZrCl_2$ (7B) | $(CH_3)_2Si(3H)$ | 0.4754(s) | |
| $^1$H | (3H) | 0.5020(s) | |
| $C_6D_6$/THF | (3H) | 0.5646(s) | |
| | (3H) | 0.5986(s) | |
| | $(CH_3)_3CH(CH_3)(9H)$ | 0.7947(s) | |
| | $(CH_3)_3CH(CH_3)(3H)$ | 1.363(d) | –6.736 |
| | $(CH_3)_2CH(3H)$ | 0.952(d) | 7.125 |
| | (3H) | 0.970(d) | 7.934 |
| | (3H) | 1.378(d) | –6.7 |
| | (3H) | 1.641(d) | 7.198 |
| | $(CH_3)_3CH(CH_3)(1H)$ | 2.892(q) | 7.106 |
| | $(CH_3)_2CH(1H)$ | 2.9124(h) | 6.742 |
| | (1H) | 2.9878(h) | 6.79 |
| | Cp—H(1H) | 6.4864(s) | |
| | (1H) | 6.657(d) | |
| | (1H) | 6.780(d) | |
| $(MNThp)ZrCl_2$ (7B) | $(CH_3)_2Si$ | –1.7099 | |
| $^{13}$C | | –1.5796 | |
| | | 3.3927 | |
| | | 3.7141 | |
| | | 15.5304 | |
| | | 20.7513 | |
| | $(CH_3)_3CH(CH_3)$, | 28.1729 | |
| | $(CH_3)_3CH(CH_3)$, | 28.5396 | |
| | $(CH_3)_2CH$, | 28.5639 | |
| | $(CH_3)_3CH(CH_3)$, and | 29.6547 | |
| | $(CH_3)_2CH$ | 29.7469 | |
| | | 34.5829 | |

-continued

$^1$H and $^{13}$C NMR Data (in $C_6D_6$, unless otherwise mentioned)

| Compound | Assignments | δ(ppm) | $J_{C-H}$ |
|---|---|---|---|
| | | 44.4194 | |
| | | 109.7364 | |
| | | 110.1156 | |
| | | 113.9873 | |
| | | 114.2007 | |
| | Cp | 115.1752 | |
| | | 134.6010 | |
| | | 137.2068 | |
| | | 140.0237 | |
| | | 163.9334 | |
| | | 166.1607 | |
| 6,6-ethyl,methyl- | $CH_3CH_2CCH_3$(3H) | 1.156(t) | 7.562 |
| fulvene | $CH_3CH_2CCH_3$(3H) | 2.1916(s) | |
| | $CH_3CH_2CCH_3$(2H) | 2.543(q) | 7.596 |
| | Cp—H(4H) | 6.44–6.52(m) | |
| Li($^t$BuCp) THF-d8 | $CH_3CH_2CHCH_3$(3H) | 1.155(d) | 6.9 |
| | $CH_3CH_2CHCH_3$(3H) | 0.839(t) | 7.5 |
| | $CH_3CH_2CCH_3$(1H) | 1.444(m) | 6.6 |
| | (1H) | 1.543(m) | 6.6 |
| | $CH_3CH_2CHCH_3$(1H) | 2.515(m) | 6.9 |
| | Cp—H(4H) | 5.526(s) | |
| $Li_2[(^iPrCp)Me_2Si—$ | $(CH_3)_2$(6H) | 0.299(s) | |
| $(^tBuCp)]$ THF-d8 | $(CH_3)_2CH$(6H) | 1.14(d) | |
| | (6H) | 1.16(d) | |
| | $CH_3CH_2CHCH_3$(3H) | 1.17(d) | |
| | $CH_3CH_2CHCH_3$(3H) | 0.853(t) | 7.2 |
| | $CH_3CH_2CCH_3$(1H) | 1.401(m) | 7.1 |
| | (1H) | 1.565(m) | 6.9 |
| | $HC_3CH_2CHCH_3$(1H) | 2.519(m) | 6.9 |
| | (1H) | 2.771(h) | 6.9 |
| | Cp—H(2H) | 3.217(h) | 6.6 |
| | (2H) | 5.817(m) | |
| | (1H) | 5.668(m) | |
| | | 5.615(m) | |
| $Li_2[(^iPr_2Cp)Me_2Si—$ | $(CH_3)_2Si$(6H) | −0.40—0.20 | |
| $(^tBuCp) = "^tBuThp"$ | (6H) | 0.35–0.8 | |
| (6) | $(CH_3)_2CH$ | | |
| | $CH_3CH_2CHCH_3$ | | |
| | $CH_3CH_2CHCH_3$(21H) | 0.8–1.8 | |
| | $CH_3CH_2CCH_3$ | | |
| | $CH_3CH_2CHCH_3$ | | |
| | $(CH_3)_2CH$(2H) | 2.4–2.9 | |
| | Cp—H(2.3H) | 3.0–4.0 | |
| | Cp—H(2.7H) | 6.35–7.1 | |

What is claimed is:

1. A metallocene of the formula

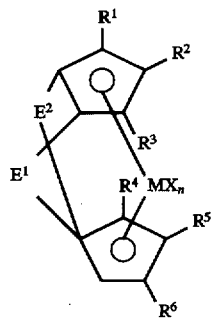

I wherein:

the metallocene has $C_S$- or $C_1$-symmetry;

M is an element selected from the group consisting of group III, group IV, group V, and lanthanide group elements;

n is the valence of M minus 2;

X is selected from the group consisting of fluorine, chlorine, bromine, iodine, hydrogen, $C_1$ to $C_{10}$ alkyl, $C_6$ to $C_{15}$ aryl, and $—OR^7$ where $R^7$ is selected from the group consisting of $C_1$ to $C_{10}$ alkyl, $C_6$ to $C_{15}$ aryl, alkylaryl, arylalkyl, fluoroalkyl, and fluoroaryl with 1 to 10 carbon atoms in the alkyl radical and 6 to 20 carbon atoms in the aryl radical;

$R^1$, $R^2$, and $R^3$ are independently selected from the group consisting of hydrogen, $C_1$ to $C_{10}$ alkyl, 5 to 7 membered cycloalkyl, which in turn may have from 1 to 3 $C_1$ to $C_{10}$ alkyls as a substituent, $C_6$ to $C_{15}$ aryl or arylalkyl wherein each pair of adjacent radicals, $R^1$ and $R^2$ or $R^2$ and $R^3$, together may also form a substituted or unsubstituted cyclic group having 4 to 15 carbon atoms, and $Si(R^8)_3$ where $R^8$ is selected from the group consisting of $C_1$ to $C_{10}$ alkyl, $C_6$ to $C_{15}$ aryl and $C_3$ to $C_{10}$ cycloalkyl;

$R^4$ and $R^6$ are substituents both having van der Waals radii that are larger than the van der Waals radii of groups $R^1$ and $R^3$;

$R^5$ is a substituent having a van der Waals radius that is less than the van der Waals radius of a methyl group; and $E^1$ and $E^2$ are independently selected from the group consisting of $Si(R^9)_2$, $Si(R^9)_2$—$Si(R^9)_2$, $Ge(R^9)_2$, $Sn(R^9)_2$, $C(R^9)_2$, and $C(R^9)_2$—$C(R^9)_2$, where $R^9$ is selected from the group consisting of $C_1$ to $C_{10}$ alkyl, $C_6$ to $C_{15}$ aryl, and $C_3$ to $C_{10}$ cycloalkyl.

2. The metallocene of claim 1, wherein M is selected from the group consisting of titanium, zirconium, hafnium, scandium, yttrium, and the lanthanides.

3. The metallocene of claim 1, wherein X is selected from the group consisting of chlorine, bromine, iodine, hydrogen, methyl, neopentyl and benzyl.

4. The metallocene of claim 1, wherein $R^4$ and $R^6$ are independently selected from the group consisting of $C_1$ to $C_{10}$ alkyl, 5 to 7 membered cycloalkyl which in turn may have a $C_1$ to $C_{10}$ alkyl as a substituent, $C_6$ to $C_{15}$ aryl or alkylaryl, and $Si(R^8)_3$.

5. The metallocene of claim 1, wherein $R^5$ is hydrogen.

6. The metallocene of claim 1, wherein $R^2$ is selected from the group consisting of hydrogen, methyl, ethyl, isopropyl, tert-butyl, phenyl, and trimethylsilyl.

7. The metallocene of claim 1, wherein $E^1$ and $E^2$ are both $Si(Me)_2$.

8. The metallocene of claim 1, wherein
M is selected from the group consisting of titanium, zirconium, hafnium, scandium, yttrium, and the lanthanides;
X is selected from the group consisting of chlorine, bromine, iodine, hydrogen, methyl, neopentyl, and benzyl;
$R^1$ and $R^3$ are the same and are selected from the group consisting of hydrogen and methyl;
$R^2$ is selected from the group consisting of hydrogen, methyl, ethyl, isopropyl, tert-butyl, trimethylsilyl, and phenyl;
$R^4$ and $R^6$ are the same and are selected from the group consisting of methyl, ethyl, isopropyl, tert-butyl, phenyl, —CH(Me)(Et), —CH(Me)($^t$Bu), neopentyl, and trimethylsilyl.

9. The metallocene of claim 8, wherein $R^4$ and $R_6$ are isopropyl; $E^1$ and $E^2$ are $Si(Me)_2$; M is selected from the group consisting of Zr and Hf; n equals 2; X is chlorine; $R^1$ and $R^3$ are hydrogen; and $R^2$ is selected from the group consisting of isopropyl and trimethylsilyl.

10. The metallocene of claim 1, wherein $R^1$ and $R^3$ are hydrogen, and $R^2$ is chiral.

11. The metallocene of claim 1, wherein
$R^1$ and $R^2$ are the same and are selected from the group consisting of $C_1$ to $C_{10}$ alkyl, 5 to 7 membered cycloalkyl, which in turn may have from 1 to 3 $C_1$ to $C_{10}$ alkyls as a substituent, $C_6$ to $C_{15}$ aryl or arylalkyl wherein $R^1$ and $R^2$ together may also form a substituted or unsubstituted cyclic group having 4 to 15 carbon atoms, and $Si(R^8)_3$ where $R^8$ is selected from the group consisting of $C_1$ to $C_{10}$ alkyl, $C_6$ to $C_{15}$ aryl, and $C_3$ to $C_{10}$ cycloalkyl; and
$R^3$ is hydrogen.

12. The metallocene of claim 11, wherein
$R^1$ and $R^2$ are the same and are selected from the group consisting of methyl, trimethylsilyl, and tert-butyl, or $R^1$ and $R^2$ together form the 6 membered ring of an indenyl, or tetrahydroindenyl.

13. The metallocene of claim 12, wherein $R^1$ and $R^2$ together form the 6 membered ring of a tetrahydroindenyl, and $R^4$ and $R^6$ are both isopropyl.

14. The metallocene of claim 1, wherein $R^1$ and $R^3$ are hydrogen, and $R^4$ and $R^6$ are different from one another.

15. The metallocene of claim 14, wherein
$R^4$ is isopropyl or tert-butyl;
$R^6$ is methyl; and $R^2$ is selected from the group consisting of $C_1$ to $C_{10}$ alkyl, and 5 to 7 membered cycloalkyl, which in turn may have from 1 to 3 $C_1$ to $C_{10}$ alkyls as a substituent.

16. A metallocene of the formula

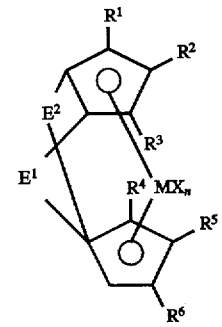

wherein:
the metallocene has $C_s$- or $C_1$-symmetry;
M is an element selected from the group consisting of group III, group IV, group V, and lanthanide group elements;
n is the valence of M minus 2;
X is selected from the group consisting of trimethylsilymethyl and bis(trimethylsilyl)methyl;
$R^1$, $R^2$, and $R^3$ are independently selected from the group consisting of hydrogen, $C_1$ to $C_{10}$ alkyl, 5 to 7 membered cycloalkyl, which in turn may have from 1 to 3 $C_1$ to $C_{10}$ alkyls as a substituent, $C_6$ to $C_{15}$ aryl or arylalkyl wherein each pair of adjacent radicals, $R^1$ and $R^2$ or $R^2$ and $R^3$, together may also form a substituted or unsubstituted cyclic group having 4 to 15 carbon atoms, and $Si(R_8)_3$ where $R^8$ is selected from the group consisting of $C_1$ to $C_{10}$ alkyl, $C_6$ to $C_{15}$ aryl and $C_3$ to $C_{10}$ cycloalkyl;
$R^4$ and $R^6$ are substituents both having van der Waals radii that are larger than the van der Waals radii of groups $R^1$ and $R_3$;
$R^5$ is a substituent having a van der Waals radius that is less than the van der Waals radius of a methyl group; and
$E^1$ and $E^2$ are independently selected from the group consisting of $Si(R^9)_2$, $Si(R^9)_2$—$Si(R^9)_2$, $Ge(R^9)_2$, $Sn(R^9)_2$, $C(R^9)_2$, and $C(R^9)_2$—$C(R^9)_2$, where $R^9$ is selected from the group consisting of $C_1$ to $C_{10}$ alkyl, $C_6$ to $C_{15}$ aryl, and $C_3$ to $C_{10}$ cycloalkyl.

17. A catalyst comprising a metal and a ligand of the formula

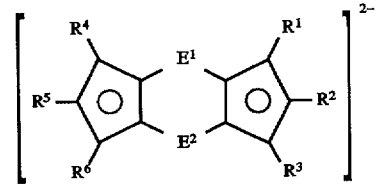

wherein:
$R^1$, $R^2$, and $R^3$ are independently selected from the group consisting of hydrogen, $C_1$ to $C_{10}$ alkyl, 5 to 7 membered cycloalkyl, which in turn may have from 1 to 3 $C_1$ to $C_{10}$ alkyls as a substituent, $C_6$ to $C_{15}$ aryl or arylalkyl wherein each pair of adjacent radicals, $R^1$ and $R^2$ or $R^2$ and $R^3$, together may also form a substituted or unsubstituted cyclic group having 4 to 15 carbon atoms, and $Si(R^8)_3$ where $R^8$ is selected from the group consisting of $C_1$ to $C_{10}$ alkyl, $C_6$ to $C_{15}$ aryl or $C_3$ to $C_{10}$ cycloalkyl;

$R^4$ and $R^6$ are substituents both having van der Waals radii larger than the van der Waals radii of groups $R^1$ and $R^3$;

$R^5$ is a substituent having a van der Waals radius that is less than the van der Waals radius of a methyl group;

$E^1$ and $E^2$ are independently selected from the group consisting of $Si(R^9)_2$, $Si(R^9)_2$—$Si(R^9)_2$, $Ge(R^9)_2$, $Sn(R^9)_2$, $C(R^9)_2$, and $C(R^9)_2$—$C(R^9)_2$, where $R^9$ is selected from the group consisting of $C_1$ to $C_{10}$ alkyl, $C_6$ to $C_{15}$ aryl, and $C_3$ to $C_{10}$ cycloalkyl.

18. The catalyst of claim 17, wherein the metal is selected from the group consisting of group III, group IV, group V and lanthanide group elements.

19. The catalyst of claim 18, wherein the metal is selected from the group consisting of titanium, zirconium, hafnium, scandium, yttrium, and the lanthanides.

20. The catalyst of claim 17, wherein $R^4$ and $R^6$ are independently selected from the group consisting of $C_1$ to $C_{10}$ alkyl, 5 to 7 membered cycloalkyl which in turn may have a $C_1$ to $C_{10}$ alkyl as a substituent, $C_6$ to $C_{15}$ aryl or alkylaryl, and $Si(R^8)_3$.

21. The catalyst of claim 17, wherein $R^5$ is hydrogen.

22. The catalyst of claim 17, wherein $R^2$ is selected from the group consisting of hydrogen, methyl, ethyl, isopropyl, tert-butyl, phenyl, and trimethylsilyl.

23. The catalyst of claim 17, wherein $E^1$ and $E^2$ are both $Si(Me)_2$.

24. The catalyst of claim 17, wherein $R^1$ and $R^3$ are the same and are hydrogen or methyl;

$R^2$ is selected from the group consisting of hydrogen, methyl, ethyl, isopropyl, tert-butyl, trimethylsilyl, and phenyl;

$R^4$ and $R^6$ are the same and are selected from the group consisting of methyl, ethyl, isopropyl, tert-butyl, phenyl, —CH(Me)(Et), —CH(Me)($^t$Bu), neopentyl, and trimethylsilyl.

25. The catalyst of claim 24, wherein $R^4$ and $R^6$ are isopropyl; $E^1$ and $E^2$ are $Si(Me)_2$; $R^1$ and $R^3$ are hydrogen; and $R^2$ is selected from the group consisting of isopropyl and trimethylsilyl.

26. The catalyst of claim 17, wherein $R^1$ and $R^3$ are hydrogen, and $R^2$ is chiral.

27. The catalyst of claim 17, wherein $R^1$ and $R^2$ are the same and are selected from the group consisting of $C_1$ to $C_{10}$ alkyl, 5 to 7 membered cycloalkyl, which in turn may have from 1 to 3 $C_1$ to $C_{10}$ alkyls as a substituent, $C_6$ to $C_{15}$ aryl or arylalkyl wherein $R^1$ and $R^2$ together may also form a substituted or unsubstituted cyclic group having 4 to 15 carbon atoms, and $Si(R^8)_3$ where $R^8$ is selected from the group consisting of $C_1$ to $C_{10}$ alkyl, $C_6$ to $C_{15}$ aryl, and $C_3$ to $C_{10}$ cycloalkyl; and $R^3$ is hydrogen.

28. The catalyst of claim 27, wherein $R^1$ and $R^2$ are the same and are selected from the group consisting of methyl, trimethylsilyl, tert-butyl, or $R^1$ and $R^2$ together form the 6 membered ring of an indenyl, or tetrahydroindenyl.

29. The catalyst of claim 28, wherein $R^1$ and $R^2$ together form the 6 membered ring of a tetrahydroindenyl, and $R^4$ and $R^6$ are both isopropyl.

30. The catalyst of claim 17, wherein $R^1$ and $R^3$ are hydrogen, and $R^4$ and $R^6$ are different from one another.

31. The catalyst of claim 30, wherein $R^4$ is isopropyl or tert-butyl;

$R^6$ is methyl; and $R^2$ is selected from the group consisting of $C_1$ to $C_{10}$ alkyl, and 5 to 7 membered cycloalkyl, which in turn may have from 1 to 3 $C_1$ to $C_{10}$ alkyls as a substituent.

32. The catalyst of claim 17, further comprising an activator.

33. The catalyst of claim 32, wherein the activator is methylaluminoxane.

34. The catalyst of claim 17, further comprising n ligands independently selected from the group consisting of fluorine, chlorine, bromine, iodine, hydrogen, $C_1$ to $C_{10}$ alkyl, $C_6$ to $C_{15}$ aryl and —$OR^7$ where $R^7$ selected from the group consisting of $C_1$ to $C_{10}$ alkyl, $C_6$ to $C_{15}$ aryl, alkylaryl, arylalkyl, fluoroalkyl, and fluoroaryl with 1 to 10 carbon atoms in the alkyl radical and 6 to 20 carbon atoms in the aryl radical; and wherein n is the valence of the metal minus 2.

35. A method for polymerizing olefins comprising the step of contacting an olefin with a catalyst comprising a metal and a ligand of the formula

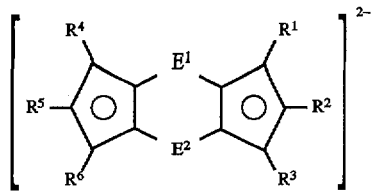

wherein:

$R^1$, $R^2$, and $R^3$ are independently selected from the group consisting of hydrogen, $C_1$ to $C_{10}$ alkyl, 5 to 7 membered cycloalkyl, which in turn may have from 1 to 3 $C_1$ to $C_{10}$ alkyls as a substituent, $C_6$ to $C_{15}$ aryl or arylalkyl wherein each pair of adjacent radicals, $R^1$ and $R^2$ or $R^2$ and $R^3$, together may also form a substituted or unsubstituted cyclic group having 4 to 15 carbon atoms, and $Si(R^8)_3$ where $R^8$ is selected from the group consisting of $C_1$ to $C_{10}$ alkyl, $C_6$ to $C_{15}$ aryl or $C_3$ to $C_{10}$ cycloalkyl;

$R^4$ and $R^6$ are substituents both having van der Waals radii larger than the van der Waals radii of groups $R^1$ and $R^3$;

$R^5$ is a substituent having a van der Waals radius less than the van der Waals radius of a methyl group;

$E^1$ and $E^2$ are independently selected from the group consisting of $Si(R^9)_2$, $Si(R^9)_2$—$Si(R^9)_2$, $Ge(R^9)_2$, $Sn(R^9)_2$, $C(R^9)_2$, and $C(R^9)_2$—$C(R^9)_2$, where $R^9$ is $C_1$ to $C_{10}$ alkyl, $C_6$ to $C_{15}$ aryl or $C_3$ to $C_{10}$ cycloalkyl.

* * * * *